US011164679B2

(12) United States Patent
Bates

(10) Patent No.: US 11,164,679 B2
(45) Date of Patent: Nov. 2, 2021

(54) SYSTEMS AND METHODS FOR INTELLIGENT PATIENT INTERFACE EXAM STATION

(71) Applicant: James Stewart Bates, Paradise Valley, AZ (US)

(72) Inventor: James Stewart Bates, Paradise Valley, AZ (US)

(73) Assignee: ADVINOW, Inc., Paradise Valley, CA (US)

( * ) Notice: Subject to any disclaimer, the term of this patent is extended or adjusted under 35 U.S.C. 154(b) by 0 days.

(21) Appl. No.: 15/628,411

(22) Filed: Jun. 20, 2017

(65) Prior Publication Data

US 2018/0365383 A1 Dec. 20, 2018

(51) Int. Cl.
*G16H 80/00* (2018.01)
*A61B 5/00* (2006.01)
(Continued)

(52) U.S. Cl.
CPC .......... *G16H 80/00* (2018.01); *A61B 5/0002* (2013.01); *G06Q 50/22* (2013.01); *G16H 10/20* (2018.01);
(Continued)

(58) Field of Classification Search
None
See application file for complete search history.

(56) References Cited

U.S. PATENT DOCUMENTS 5,158,088 A 10/1992 Nelson et al.
5,839,438 A 11/1998 Graettinger et al.
(Continued)

FOREIGN PATENT DOCUMENTS

CN 1293752 A 5/2001
CN 1422369 A 6/2003
(Continued)

OTHER PUBLICATIONS

DigiO2, The healthcare kiosk of digiO2, Published Apr. 25, 2012, Youtube, https://www.youtube.com/watch?v=s6Oulo7ljSA (Year: 2012).*

(Continued)

*Primary Examiner* — Jonathan T Kuo
(74) *Attorney, Agent, or Firm* — North Weber & Baugh LLP; Michael North

(57) ABSTRACT

Presented are systems and methods for examining patients and generating diagnostic medical data to make automated diagnoses and treatment recommendations to patients and doctors. Various embodiments of the present invention provide patients with diagnostic tools and audio/video guidance to reliably and accurately perform clinical grade diagnostic measurements of key vital signs. In embodiments, this is accomplished by using an automated remote (or local, e.g., in the form of a kiosk) end-to-end medical diagnostic system that monitors equipment usage for accuracy. The diagnostic system analyzes patient responses, measurement data, and patient-related information to generate diagnostic and/or treatment information that may be shared with healthcare professionals and specialists, as needed. Automation provides for timely, hassle-free, and cost-effective health care management that takes the stress out of doctor visits, while delivering personalized health care. The high accuracy of generated diagnostic data improves health care to patients and reduces the risk of medical malpractice for treating physicians.

19 Claims, 5 Drawing Sheets

(51) Int. Cl.
*G06Q 50/22* (2018.01)
*G16H 40/63* (2018.01)
*G16H 50/20* (2018.01)
*G16H 10/20* (2018.01)
*G16H 30/20* (2018.01)
*G16H 40/20* (2018.01)
*H04N 7/14* (2006.01)
*A61B 5/0205* (2006.01)

(52) U.S. Cl.
CPC ............ *G16H 30/20* (2018.01); *G16H 40/20* (2018.01); *G16H 40/63* (2018.01); *G16H 50/20* (2018.01); *A61B 5/0022* (2013.01); *A61B 5/02055* (2013.01); *H04N 7/141* (2013.01)

(56) References Cited

U.S. PATENT DOCUMENTS

| | | |
|---|---|---|
| 6,205,716 B1 | 3/2001 | Peltz |
| 6,246,898 B1 | 6/2001 | Vesely et al. |
| 6,607,480 B1 | 8/2003 | Bousseljot et al. |
| 6,915,254 B1 | 7/2005 | Heinze et al. |
| 6,970,742 B2 | 11/2005 | Mann et al. |
| 7,149,756 B1 | 12/2006 | Schmitt et al. |
| 7,171,311 B2 | 1/2007 | Dai et al. |
| 7,197,492 B2 * | 3/2007 | Sullivan ............. G06Q 10/10 |
| 7,302,288 B1 | 11/2007 | Schellenberg |
| 7,384,146 B2 | 6/2008 | Covannon et al. |
| 7,613,502 B2 | 11/2009 | Yamamoto et al. |
| 7,627,489 B2 | 12/2009 | Schaeffer et al. |
| 8,043,224 B2 | 10/2011 | Sarel |
| 8,126,735 B2 | 2/2012 | Dicks et al. |
| 8,140,154 B2 | 3/2012 | Donnelly et al. |
| 8,275,442 B2 | 9/2012 | Allison |
| 8,358,822 B2 | 1/2013 | Sun et al. |
| 8,463,346 B2 | 6/2013 | Kuhn et al. |
| 8,548,828 B1 | 10/2013 | Longmire |
| 9,460,400 B2 | 10/2016 | De Bruin et al. |
| 9,552,745 B1 | 1/2017 | Gutierrez Morales |
| 9,697,828 B1 | 7/2017 | Prasad et al. |
| 10,143,373 B2 * | 12/2018 | Gilad-Gilor ......... A61B 5/0077 |
| 2001/0021801 A1 | 9/2001 | Bardy |
| 2001/0029322 A1 | 10/2001 | Iliff |
| 2002/0065455 A1 | 5/2002 | Ben-Haim et al. |
| 2002/0065457 A1 | 5/2002 | Kuth |
| 2002/0165448 A1 | 11/2002 | Ben-Haim et al. |
| 2003/0028406 A1 | 2/2003 | Herz et al. |
| 2003/0216937 A1 | 11/2003 | Schreiber et al. |
| 2004/0024309 A1 | 2/2004 | Ferre et al. |
| 2005/0054938 A1 | 3/2005 | Wehman et al. |
| 2005/0075907 A1 | 4/2005 | Rao |
| 2005/0165285 A1 | 7/2005 | Iliff |
| 2005/0251030 A1 | 11/2005 | Azar et al. |
| 2005/0256395 A1 | 11/2005 | Anabuki et al. |
| 2006/0036619 A1 | 2/2006 | Fuerst et al. |
| 2006/0111620 A1 | 5/2006 | Squilla et al. |
| 2006/0138288 A1 | 6/2006 | Parsons |
| 2006/0173712 A1 | 8/2006 | Joubert |
| 2006/0270918 A1 | 11/2006 | Stupp et al. |
| 2006/0271400 A1 | 11/2006 | Clements et al. |
| 2007/0100666 A1 * | 5/2007 | Stivoric ............... A61B 5/6833 705/3 |
| 2007/0104316 A1 | 5/2007 | Ruchala et al. |
| 2007/0150313 A1 | 6/2007 | Abraham-Fuchs et al. |
| 2007/0168233 A1 | 7/2007 | Hymel |
| 2007/0244702 A1 | 10/2007 | Kahn et al. |
| 2007/0265542 A1 | 11/2007 | Bardy |
| 2008/0058945 A1 | 3/2008 | Hajaj et al. |
| 2008/0068197 A1 | 3/2008 | Neubauer et al. |
| 2008/0071578 A1 | 3/2008 | Herz et al. |
| 2008/0081973 A1 | 4/2008 | Hoarau |
| 2008/0183030 A1 | 7/2008 | Shiri et al. |
| 2008/0228528 A1 | 9/2008 | Keen et al. |
| 2008/0275738 A1 | 11/2008 | Shillingburg |
| 2009/0030382 A1 | 1/2009 | Brandt et al. |
| 2009/0062623 A1 | 3/2009 | Cohen et al. |
| 2009/0062670 A1 | 3/2009 | Sterling et al. |
| 2009/0094059 A1 | 4/2009 | Coleman et al. |
| 2009/0187425 A1 | 7/2009 | Thompson |
| 2009/0240524 A1 | 9/2009 | Bluth |
| 2009/0299766 A1 | 12/2009 | Friedlander et al. |
| 2009/0299767 A1 | 12/2009 | Michon et al. |
| 2010/0023351 A1 | 1/2010 | Lifshits et al. |
| 2010/0057651 A1 | 3/2010 | Fung et al. |
| 2010/0280350 A1 | 11/2010 | Zhang |
| 2010/0298899 A1 | 11/2010 | Donnelly et al. |
| 2011/0053128 A1 | 3/2011 | Alman |
| 2011/0087135 A1 | 4/2011 | Ferzli et al. |
| 2011/0112793 A1 | 5/2011 | Diebold et al. |
| 2011/0166465 A1 | 7/2011 | Clements et al. |
| 2011/0201962 A1 | 8/2011 | Grudic et al. |
| 2011/0202370 A1 | 8/2011 | Green, III et al. |
| 2011/0225002 A1 | 9/2011 | Fackler et al. |
| 2011/0237963 A1 | 9/2011 | Nishioka et al. |
| 2011/0295621 A1 | 12/2011 | Farooq et al. |
| 2012/0022348 A1 | 1/2012 | Droitcour et al. |
| 2012/0065987 A1 | 3/2012 | Farooq et al. |
| 2012/0078062 A1 | 3/2012 | Bagchi et al. |
| 2012/0084092 A1 | 4/2012 | Kozuch et al. |
| 2012/0191476 A1 | 7/2012 | Reid et al. |
| 2012/0232930 A1 | 9/2012 | Schmidt et al. |
| 2012/0247472 A1 | 10/2012 | Lynch, Jr. |
| 2012/0289825 A1 | 11/2012 | Rai et al. |
| 2012/0323592 A1 | 12/2012 | Bechtel et al. |
| 2013/0185099 A1 | 7/2013 | Bucur et al. |
| 2013/0226601 A1 | 8/2013 | Razmi et al. |
| 2013/0237811 A1 | 9/2013 | Mihailescu et al. |
| 2013/0253940 A1 | 9/2013 | Zziwa |
| 2013/0268203 A1 | 10/2013 | Pyloth |
| 2013/0289362 A1 | 10/2013 | Kruglick et al. |
| 2013/0297217 A1 | 11/2013 | Bangera et al. |
| 2013/0297348 A1 | 11/2013 | Cardoza et al. |
| 2013/0338447 A1 * | 12/2013 | Gilad-Gilor ......... A61B 5/0077 600/300 |
| 2014/0052463 A1 | 2/2014 | Cashman et al. |
| 2014/0058755 A1 * | 2/2014 | Macoviak ............. G06F 19/328 705/3 |
| 2014/0074454 A1 | 3/2014 | Brown et al. |
| 2014/0095201 A1 | 4/2014 | Farooq et al. |
| 2014/0100885 A1 | 4/2014 | Stern |
| 2014/0236630 A1 | 8/2014 | Murata |
| 2014/0244278 A1 | 8/2014 | Park et al. |
| 2014/0275928 A1 | 8/2014 | Acquista et al. |
| 2014/0257047 A1 | 9/2014 | Sillay et al. |
| 2014/0257852 A1 | 9/2014 | Walker et al. |
| 2014/0266787 A1 | 9/2014 | Tran |
| 2014/0275849 A1 | 9/2014 | Acquista |
| 2014/0276552 A1 | 9/2014 | Nguyen, Jr. et al. |
| 2014/0279746 A1 | 9/2014 | De Bruin et al. |
| 2014/0303680 A1 | 10/2014 | Donnelly et al. |
| 2014/0324453 A1 | 10/2014 | Herz et al. |
| 2014/0359722 A1 | 12/2014 | Schultz et al. |
| 2015/0019257 A1 | 1/2015 | Doyle et al. |
| 2015/0031964 A1 | 1/2015 | Bly et al. |
| 2015/0087926 A1 | 3/2015 | Raz et al. |
| 2015/0094605 A1 | 4/2015 | Sabesan et al. |
| 2015/0111220 A1 | 4/2015 | Blume et al. |
| 2015/0120321 A1 | 4/2015 | David et al. |
| 2015/0213194 A1 | 7/2015 | Wolf et al. |
| 2015/0227620 A1 | 8/2015 | Takeuchi et al. |
| 2015/0238107 A1 | 8/2015 | Acquista et al. |
| 2015/0244687 A1 | 8/2015 | Perez et al. |
| 2015/0248536 A1 | 9/2015 | Tawil et al. |
| 2015/0265217 A1 * | 9/2015 | Penders ................ A61B 5/00 600/301 |
| 2015/0347385 A1 | 12/2015 | Flor et al. |
| 2016/0000515 A1 | 1/2016 | Sela et al. |
| 2016/0023046 A1 | 1/2016 | Evin et al. |
| 2016/0038092 A1 | 2/2016 | Golay |
| 2016/0067100 A1 | 3/2016 | Cottler et al. |
| 2016/0098542 A1 | 4/2016 | Costantini et al. |
| 2016/0110523 A1 | 4/2016 | Francois |

(56) References Cited

U.S. PATENT DOCUMENTS

| | | | |
|---|---|---|---|
| 2016/0140318 A1* | 5/2016 | Stangel | G06F 19/3481 705/3 |
| 2016/0267222 A1 | 9/2016 | Larcom et al. | |
| 2016/0302710 A1 | 10/2016 | Alberts et al. | |
| 2016/0342753 A1 | 11/2016 | Feazell | |
| 2017/0011172 A1 | 1/2017 | Rauchel | |
| 2017/0020382 A1 | 1/2017 | Sezan et al. | |
| 2017/0039502 A1 | 2/2017 | Guman et al. | |
| 2017/0079580 A1 | 3/2017 | Moore et al. | |
| 2017/0084036 A1 | 3/2017 | Pheiffer et al. | |
| 2017/0105650 A1 | 4/2017 | Peacock, III et al. | |
| 2017/0105802 A1 | 4/2017 | Taraschi et al. | |
| 2017/0109501 A1 | 4/2017 | Eid | |
| 2017/0154212 A1 | 6/2017 | Feris et al. | |
| 2017/0169171 A1 | 6/2017 | Loeb et al. | |
| 2017/0173262 A1 | 6/2017 | Veltz | |
| 2017/0199987 A1 | 7/2017 | Loeb et al. | |
| 2017/0228517 A1 | 8/2017 | Saliman et al. | |
| 2017/0262614 A1 | 9/2017 | Vishnubhatla et al. | |
| 2017/0323064 A1 | 11/2017 | Bates | |
| 2017/0323071 A1 | 11/2017 | Bates | |
| 2017/0344711 A1 | 11/2017 | Liu et al. | |
| 2018/0025121 A1 | 1/2018 | Fei et al. | |
| 2018/0046773 A1 | 2/2018 | Tang et al. | |
| 2018/0121857 A1 | 5/2018 | Gutman et al. | |
| 2018/0192965 A1 | 7/2018 | Rose et al. | |
| 2018/0235709 A1 | 8/2018 | Donhowe et al. | |
| 2018/0322249 A1 | 11/2018 | Allen et al. | |
| 2018/0322251 A1 | 11/2018 | Allen et al. | |
| 2018/0330058 A1 | 11/2018 | Bates | |
| 2018/0330059 A1 | 11/2018 | Bates et al. | |
| 2018/0330062 A1 | 11/2018 | Balaban et al. | |
| 2019/0095957 A1 | 3/2019 | Ibarria et al. | |
| 2019/0139648 A1 | 5/2019 | Rutledge et al. | |
| 2019/0180873 A1 | 6/2019 | Kartoun et al. | |
| 2019/0274523 A1 | 9/2019 | Bates et al. | |
| 2019/0355149 A1 | 11/2019 | Avendi et al. | |
| 2020/0167834 A1 | 5/2020 | Matsuoka et al. | |
| 2020/0405433 A1 | 12/2020 | Sela et al. | |

FOREIGN PATENT DOCUMENTS

| | | |
|---|---|---|
| CN | 1765317 A | 5/2006 |
| CN | 1774206 A | 5/2006 |
| CN | 102245087 A | 11/2009 |
| CN | 201399700 Y | 2/2010 |
| CN | 103281370 A | 9/2013 |
| CN | 103828360 A | 5/2014 |
| CN | 104363831 A | 2/2015 |
| CN | 104684461 A | 5/2018 |
| CN | 104000654 A | 7/2018 |
| EP | 1316039 | 1/2002 |
| TW | 201629895 A | 8/2016 |
| WO | 9904043 A1 | 1/1999 |
| WO | 02001470 A1 | 1/2002 |
| WO | 2014088933 A1 | 6/2014 |
| WO | 2016178973 A1 | 11/2016 |
| WO | 2017192918 A1 | 11/2017 |

OTHER PUBLICATIONS

International Search Report dated Jul. 26, 2017, in International Patent Application No. PCT/US2017/031158, filed May 4, 2017 (5 pgs).

Written Opinion dated Jul. 26, 2017, in International Patent Application No. PCT/US2017/031158, filed May 4, 2017 (5 pgs).

International Search Report dated Jul. 20, 2017, in International Patent Application No. PCT/US2017/031159, filed May 4, 2017 (6 pgs).

Written Opinion dated Jul. 20, 2017, in International Patent Application No. PCT/US2017/031159, filed May 4, 2017 (9 pgs).

International Search Report dated Aug. 1, 2017, in International Patent Application No. PCT/US2017/031163, filed May 4, 2017 (6 pgs).

Written Opinion dated Aug. 1, 2017, in International Patent Application No. PCT/US2017/031163, filed May 4, 2017 (7 pgs).

International Search Report and Written Opinion dated Jul. 27, 2018, in International Patent Application No. PCT/US2018/030989, filed May 3, 2018 (6 pgs).

International Search Report and Written Opinion dated Jul. 27, 2018, in International Patent Application No. PCT/US2018/30991, filed May 3, 2018 (6 pgs).

International Search Report dated Aug. 23, 2018, in international Patent Application No. PCT/US18/37163, filed Jun. 12, 2018 (2 pgs).

Written Opinion dated Aug. 23, 2018, in international Patent Application No. PCT/US18/37163, filed Jun. 12, 2018 (9 pgs).

Non-Final Office Action dated Nov. 8, 2018, in related U.S. Appl. No. 15/344,390 (23 pgs).

Response filed Dec. 6, 2018, in related U.S. Appl. No. 15/344,390 (18 pgs).

International Search Report and Written Opinion dated Apr. 15, 2019 in International Patent Application No. PCT/US19/12166, filed Jan. 3, 2019 (14 pgs).

International Search Report and Written Opinion dated Apr. 11, 2019 in International Patent Application No. PCT/US19/12901, filed Jan. 9, 2019 (7 pgs).

Non-Final Office Action dated Feb. 21, 2019, in U.S. Appl. No. 15/352,488 (31 pgs).

Response to Non-Final Office Action filed Feb. 26, 2019, in U.S. Appl. No. 15/352,488 (17 pgs).

Non-Final Office Action dated May 15, 2019, in U.S. Appl. No. 15/590,721, (48 pgs).

International Search Report and Written Opinion dated May 13, 2019, in International Application No. PCT/US2019/020848, filed Mar. 5, 2019 (8 pgs).

International Search Report and Written Opinion dated May 17, 2019, in International Application No. PCT/US2019/020844, filed Mar. 5, 2019 (14 pgs).

Non-Final Office Action dated May 14, 2019, in U.S. Appl. No. 15/590,997, (42 pgs).

Non-Final Office Action dated May 2, 2019, in U.S. Appl. No. 15/344,390, (19 pgs).

Non-Final Office Action Response filed Jun. 4, 2019, in U.S. Appl. No. 15/590,997, (13 pgs).

Non-Final Office Action Response filed Jul. 30, 2019, in U.S. Appl. No. 15/590,721, (16 pgs).

International Search Report and Written Opinion dated Jun. 14, 2019, in International Application No. PCT/US2019/020845, filed Mar. 5, 2019 (7 pgs).

Non-Final Office Action Response filed Jul. 30, 2019, in U.S. Appl. No. 15/344,390, (9 pgs).

Final Office Action dated Jun. 20, 2019, in U.S. Appl. No. 15/352,488, (24 pgs).

Video available from the Internet at <URL: https://www.azbio.tv/video/1173cba2664c41078b757f11f2d5073b>, "AdviNow Medical—2018 Fast Lane Honoree", by AZBio, published on Oct. 6, 2018. (1 pg).

Non-Final Office Action dated Jul. 17, 2019, in U.S. Appl. No. 15/355,472, (43 pgs).

Non-Final Office Action dated Jul. 17, 2019, in U.S. Appl. No. 15/371,000, (37 pgs).

Supplemental Response to Non-Final Office Action filed Aug. 20, 2019 in U.S. Appl. No. 15/344,390, 9 pgs.

Response to Final Office Action & Request for Continued Examination (RCE), filed Aug. 20, 2019 in U.S. Appl. No. 15/352,488, 9 pgs.

Non-Final Office Action Response filed Oct. 17, 2019, in related U.S. Appl. No. 15/355,472, (12 pgs).

Non-Final Office Action Response filed Oct. 17, 2019, in related U.S. Appl. No. 15/371,000, (9 pgs).

Final Office Action dated Sep. 16, 2019, in related U.S. Appl. No. 15/590,997, (55 pgs).

(56) References Cited

OTHER PUBLICATIONS

Non-Final Office Action dated Sep. 23, 2019, in related U.S. Appl. No. 16/170,775, (39 pgs).
Final Office Action dated Oct. 8, 2019, in related U.S. Appl. No. 15/590,721, (67 pgs).
Response to Final Office Action dated Nov. 5, 2019, in related U.S. Appl. No. 15/590,721, (14 pgs).
Non-Final Office Action dated Oct. 29, 2019, in related U.S. Appl. No. 15/863,078, (74 pgs).
Response to Final Office Action filed Nov. 15, 2019, in related U.S. Appl. No. 115/590,997, (12 pgs).
Response to Non-Final Office Action filed Nov. 21, 2019, in related U.S. Appl. No. 16/170,775, (14 pgs).
Final Office Action dated Dec. 5, 2019, in related U.S. Appl. No. 15/344,390, (35 pgs).
Supplementary Search Report dated Nov. 27, 2019, in related European application No. EP 17 79 3393, (15 pgs).
Advisory Action dated Nov. 29, 2019, in related U.S. Appl. No. 15/590,721, (3 pgs).
Response to Final Office Action and RCE filed on Jan. 16, 2020, in related U.S. Appl. No. 15/590,721, (15 pgs).
Advisory Action dated Dec. 5, 2019, in related U.S. Appl. No. 15/590,997, (3 pgs).
Response to Final Office Action and RCE filed on Jan. 16, 2020, in related U.S. Appl. No. 15/590,997, (12 pgs).
Non-Final Office Action dated Jan. 30, 2020, in related U.S. Appl. No. 15/352,488, (13 pgs).
Final Office Action dated Jan. 31, 2020, in related U.S. Appl. No. 15/355,472, (19 pgs).
Final Office Action dated Jan. 30, 2020, in related U.S. Appl. No. 15/371,000, (17 pgs).
Applicant-Initiated Interview Summary dated Jan. 31, 2020, in related U.S. Appl. No. 15/863,078, (8 pgs).
Applicant-Initiated Interview Summary dated Nov. 18, 2019, in related U.S. Appl. No. 15/352,488, (3 pgs).
Final Office Action dated Mar. 30, 2021 in related U.S. Appl. No. 15/913,780, (13 pgs).
Appeal Brief filed on May 8, 2020 and Notice of Allowance dated Nov. 6, 2020 in related U.S. Appl. No. 15/344,390, (43 pgs).
Supplementary European Search Report dated Jan. 20, 2020 in related European application No. 17793389.2, (10 pgs).
Response to Non-Final Office Action filed Jul. 26, 2020, Final Office Action dated Oct. 28, 2020, Response filed Dec. 29, 2020, Advisory Action dated Feb. 22, 2021, Appeal Notice filed Mar. 1, 2021, in related U.S. Appl. No. 15/352,488, (48 pgs).
Supplementary European Search Report dated Feb. 1, 2020 in related European application No. 17793390.0, (10 pgs).
Final Office Action dated Mar. 12, 2020 in related U.S. Appl. No. 16/170,775, and Response filed on Sep. 29, 2020 (30 pgs).
Response to Final Office Action filed Jul. 26, 2020, Non-Final Office Action dated Mar. 8, 2021 in related U.S. Appl. No. 15/355,472, (25 pgs).
Non-Final Office Action dated Jan. 11, 2021 in related U.S. Appl. No. 15/371,000, (13 pgs).
Non-Final Office Action dated May 15, 2020, response filed Feb. 4, 2021, in related U.S. Appl. No. 15/590,997, (54 pgs).
Non-Final Office Action dated Feb. 21, 2020, response filed Aug. 2, 2020, Non-Final Office Action dated Nov. 10, 2020, response filed Feb. 4, 2021, in related U.S. Appl. No. 15/709,007, and Response filed Aug. 2, 2020 (96 pgs).
Non-Final Office Action dated Mar. 3, 2020, Response filed Sep. 29, 2020, Non-Final Office Action dated Jan. 26, 2021, Response filed Mar. 23, 2021, in related U.S. Appl. No. 15/590,721, (144 pgs).
Restriction Requirement dated Feb. 6, 2020, response filed Aug. 2, 2020, Non-Final Office Action dated Oct. 7, 2020, response filed Jan. 7, 2021, in related U.S. Appl. No. 15/913,780, and Response filed on Aug. 2, 2020, (92 pgs).
Restriction Requirement dated Jun. 4, 2020, response filed Jun. 5, 2020, Non-Final Office Action dated Jul. 7, 2020, response filed Aug. 14, 2020, Notice of Allowance dated Oct. 21, 2020 in related U.S. Appl. No. 15/913,801, (92 pgs).
Final Office Action dated Feb. 12, 2020, response filed Feb. 4, 2021, in related U.S. Appl. No. 15/863,078, (46 pgs).
Non-Final Office Action dated Jul. 8, 2020, response filed Feb. 4, 2021, in related U.S. Appl. No. 15/872,274, (95 pgs).
Office Action dated Jan. 6, 2021 in related Chinese application No. 201780037959.4, response filed Feb. 11, 2021, (23 pgs).
Office Action dated Feb. 1, 2021 in related Chinese application No. 201780034877.4, (35 pgs).
Non-Final Office Action dated Apr. 21, 2021, in related U.S. Appl. No. 15/863,078, (41 pgs).
Final Office Action dated Apr. 26, 2021, in related U.S. Appl. No. 15/709,007, (19 pgs).
Final Office Action Response filed Jun. 25, 2021, in related U.S. Appl. No. 15/709,007, (12 pgs).
Advisory Action dated Jul. 16, 2021, in related U.S. Appl. No. 15/709,007, (3 pgs).
Advisory Action dated Jun. 3, 2021, in related U.S. Appl. No. 15/913,780, (4 pgs).
Advisory Action Response filed Jun. 29, 2021, in related U.S. Appl. No. 15/913,780, (13 pgs).
Response to Office Action filed Aug. 17, 2021, in related European application No. 17793389.2-1126, (12 pgs).
Response to Office Action filed Aug. 17, 2021, in related European application No. 17793390.0-1126, (8 pgs).
Response to Office Action filed Jun. 10, 2021, in related Chinese application No. 201780034877.4, (17 pgs).
Office Action dated Jun. 23, 2021, and response to office action filed Jul. 16, 2021 in related Chinese application No. 201780037959.4, (24 pgs).
Response to the Search & Written Opinion filed on Jul. 16, 2021, in related European application No. 18 799 372.0-1126, (8 pgs).
Non-Final office action response filed Jul. 21, 2021; final office action dated Sep. 10, 2021; notice of appeal filed Sep. 20, 2021, in related U.S. Appl. No. 15/863,078, (53 pgs).
Non-Final office action dated Jul. 28, 2021; response filed Sep. 20, 2021, in related U.S. Appl. No. 15/590,721, (66 pgs).
Final office action response filed Jul. 26, 2021 in related U.S. Appl. No. 15/709,007, (12 pgs).
Final office action dated Aug. 9, 2021; response filed Sep. 16, 2021, in related U.S. Appl. No. 15/371,000, (34 pgs).
Chinese office action dated Jul. 29, 2021 in related Chinese patent application No. 201780034877.4 (22 pgs).
Final office action dated Aug. 2, 2021; notice of appeal filed Sep. 20, 2021, in related U.S. Appl. No. 15/872,274, (81 pgs).
Restriction Requirement dated Aug. 3, 2021; response filed Sep. 20, 2021, in related U.S. Appl. No. 15/913,822, (15 pgs).
Appeal brief filed Aug. 9, 2021, in related U.S. Appl. No. 15/355,472, (36 pgs).
Office action response filed Aug. 20, 2021, in related European application No. EP18820668.4, (8 pgs).
Final office action response filed Sep. 7, 2021 in related U.S. Appl. No. 15/590,997, (10 pgs).
Office action response filed Sep. 9, 2021, in related European application No. EP18798764.9, (12 pgs).
Office action dated Sep. 13, 2021 in European patent application No. EP18799372.0, (10 pgs).

* cited by examiner

SYSTEMS AND METHODS FOR INTELLIGENT PATIENT INTERFACE EXAM STATION

BACKGROUND

Technical Field

The present disclosure relates to health care, and more particularly, to systems and methods for automatically examining patients and generating diagnostic medical data and treatment recommendations.

Background of the Invention

The inconvenience of scheduling an appointment with a physician or other health care provider in a time-efficient manner is causing a gradual shift away from patients establishing and relying on a life-long relationship with a single general practitioner to diagnoses and treat the patient in health-related matters, towards patients opting to receive readily available treatment in more conveniently located urgent care facilities that provide relatively easy access to health care without the hassle of scheduling appointments oftentimes weeks or months ahead of time. Yet, the decreasing importance of primary doctors makes it difficult for different treating physicians to maintain a reasonably complete medical record for each patient, which results in patients having to repeat a great amount of personal and medical information each time when visiting a different health care facility or doctor. In some cases, patients confronted with lengthy and time-consuming patient questionnaires fail to provide accurate information that may be important for a proper medical treatment, be it for the sake of expediting their visit or other reasons. In addition, studies have shown that patients attending urgent care or emergency facilities may, in fact, worsen their health conditions due to the risk of exposure to bacteria or viruses in medical facilities despite the medical profession's efforts to minimize the number of such instances.

Through consistent regulation changes, electronic health record changes and pressure from payers, both health care facilities and providers are looking for ways to make patient intake, triage, diagnosis, treatment, electronic health record data entry, treatment, billing, and patient follow-up activity more efficient, provide better patient experience, and increase the doctors' patient throughput, while reducing cost.

The desire to increase access to health care providers, a pressing need to reduce health care costs in developed countries, and the goal of making health care available to a larger population in less developed countries all have fueled the idea of telemedicine. In most cases, however, video or audio conferencing with a doctor does not provide sufficient patient-physician interaction necessary to allow for a proper medical diagnosis to efficiently serve patients' needs.

What is needed are systems and methods that ensure reliable remote or local medical patient intake, triage, diagnosis, treatment, electronic health record data entry/management, treatment, billing, and patient follow-up activity, so that physicians can allocate patient time more efficiently and, in some instances, allow individuals to manage their own health, thereby, reducing the overall cost of health care.

BRIEF DESCRIPTION OF THE DRAWINGS

References will be made to embodiments of the invention, examples of which may be illustrated in the accompanying figures. These figures are intended to be illustrative, not limiting. Although the invention is generally described in the context of these embodiments, it should be understood that it is not intended to limit the scope of the invention to these particular embodiments.

DETAILED DESCRIPTION OF THE PREFERRED EMBODIMENTS

Figure 1:
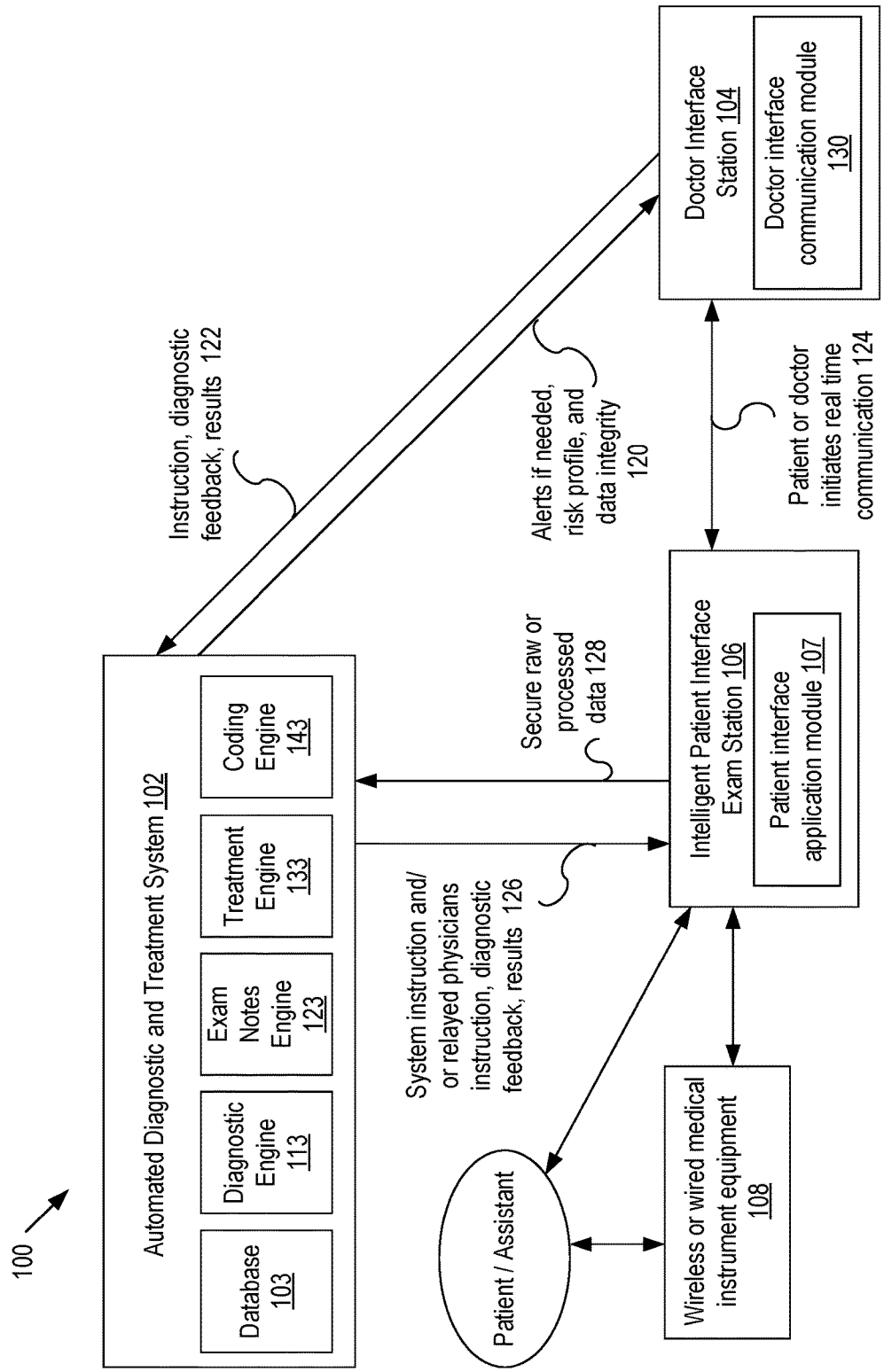
FIG. 1 illustrates an exemplary diagnostic system according to embodiments of the present disclosure.

In the following description, for purposes of explanation, specific details are set forth in order to provide an understanding of the disclosure. It will be apparent, however, to one skilled in the art that the disclosure can be practiced without these details. Furthermore, one skilled in the art will recognize that embodiments of the present disclosure, described below, may be implemented in a variety of ways, such as a process, an apparatus, a system, a device, or a method on a tangible computer-readable medium.

Elements/components shown in diagrams are illustrative of exemplary embodiments of the disclosure and are meant to avoid obscuring the disclosure. It shall also be understood that throughout this discussion that components may be described as separate functional units, which may comprise sub-units, but those skilled in the art will recognize that various components, or portions thereof, may be divided into separate components or may be integrated together, including integrated within a single system or component. It should be noted that functions or operations discussed herein may be implemented as components/elements. Components/elements may be implemented in software, hardware, or a combination thereof.

Furthermore, connections between components or systems within the figures are not intended to be limited to direct connections. Rather, data between these components may be modified, re-formatted, or otherwise changed by intermediary components. Also, additional or fewer connections may be used. Also, additional or fewer connections may be used. It shall also be noted that the terms "coupled" "connected" or "communicatively coupled" shall be understood to include direct connections, indirect connections through one or more intermediary devices, and wireless connections.

Reference in the specification to "one embodiment," "preferred embodiment," "an embodiment," or "embodiments" means that a particular feature, structure, characteristic, or function described in connection with the embodiment is included in at least one embodiment of the disclosure and may be in more than one embodiment. The appearances of the phrases "in one embodiment," "in an embodiment," or "in embodiments" in various places in the specification are not necessarily all referring to the same embodiment or embodiments. The terms "include," "including," "comprise," and "comprising" shall be understood to be open terms and any lists that follow are examples and not meant to be limited to the listed items. Any headings used herein are for organizational purposes only and shall not be used to limit the scope of the description or the claims.

Furthermore, the use of certain terms in various places in the specification is for illustration and should not be construed as limiting. A service, function, or resource is not limited to a single service, function, or resource; usage of these terms may refer to a grouping of related services, functions, or resources, which may be distributed or aggregated.

In this document, the term "kiosk" or "patient interface station" refers to any device or combination of devices, including devices such as mobile devices (e.g., tablets), for gathering and processing data to generate and display medical data (e.g., vital signs data). The term "sensor" refers to a device capable of acquiring information related to any type of physiological condition or activity (e.g., a biometric diagnostic sensor); physical data (e.g., a weight); and environmental information (e.g., ambient temperature sensor), including hardware-specific information. The term "position" refers to spatial and temporal data (e.g., orientation and motion information). "Doctor" refers to any health care professional, health care provider, physician, or person directed by a physician. "Patient" is any user who uses the systems and methods of the present invention, e.g., a person being examined or anyone assisting such person. The term illness may be used interchangeably with the term diagnosis. As used herein, "answer" or "question" refers to one or more of 1) an answer to a question, 2) a measurement or measurement request (e.g., a measurement performed by a "patient"), and 3) a symptom (e.g., a symptom selected by a "patient").

FIG. 1 illustrates an exemplary diagnostic system according to embodiments of the present disclosure. Diagnostic system 100 comprises automated diagnostic and treatment system 102, intelligent patient interface exam station 106, doctor interface station 104, and medical instrument equipment 108. Both patient interface station 106 and doctor interface station 104 may comprise a graphical user interface (GUI) and may be implemented into a tablet, computer, mobile device, or other electronic device. Different GUIs may be used based on user authorization level and may provide different screen views to users (e.g., patients, doctors/nurses, operation managers, and administrators). The GUI may work with any number of input devices (e.g., touch screen, keyboard, sensors) and may be optimized for easily and efficiently providing data (e.g., language selection, authentication/registration), and may provide audio/visual instructions on measurements (e.g., animation view and real time stream of the user).

In embodiments, kiosk comprises a high-resolution camera that may be positioned to capture a patient's head and/or body. In embodiments, kiosk comprises communication system that may enable a secure intranet connection to a remote server, e.g., via an Ethernet or a Wi-Fi connection.

In embodiments, patient interface station 106 and/or doctor interface station 104 utilize a core backend program that outlines program calls, e.g., in the form of an application library wrapped in the interface. A backend library may interface through a measurement API that, in turn, may call individual sensor drivers. Intelligent patient interface exam station 106 and/or doctor interface station 104 may be used to login or register a new account, verify or update medical information, answer health-related questions, and perform initial self-measurements to be recorded for each session or visit. In embodiments, a login state determines the validity of a format of an answer and may provide instructions on how to make corrections. The login state may allow a user to create an account, and logs any valid and failed authentication attempts, including username, time of the attempt, the interface being accessed, and a kiosk ID. In embodiments, after a certain number of failed attempts to connect to a sensor or a timeout event triggered by a watchdog timer, if an allotted measurement time is exceeded, the interface station may raise an exception.

Once logged in, kiosk may enter a next state or mode of operation, e.g., a patient mode, in which kiosk may take patient personal and health information, financial information, chief complaint information, baseline measurements and ask follow up questions. In embodiments, in response to receiving answers to a patient's past medical history (e.g., regarding allergies, smoking habits, caffeine usage), kiosk accesses, in real time, a database to retrieve possible questions and related choices that kiosk displays at an interface to enable the patient to make a selection from possible choices related to each answer. In the event of no activity a timeout may end or restart a session. In embodiments, an exception mode of operation is used to detect and record an unexpected condition and cause kiosk to terminate its current session.

In embodiments, intelligent patient interface exam station 106 may provide a landing screen that inquires whether a patient's information has recently changed or should be updated. Intelligent patient interface exam station 106 may prompt a user for a patient ID/insurance card to identify a patient and may ask initial questions, e.g., via a search field for health concerns that may use a key-based search, prior to instructing the user to take self-measurements.

In embodiments, based on patient-interaction, automated diagnostic and treatment system 102 may determine its next state, mode of operation, tasks, or next steps of patient-interaction (e.g., questions to answer, measurements to take). In embodiments, for example, upon automated diagnostic and treatment system 102 verifying user credentials, a session ID may be generated for each session and communicated, e.g., together with patient answers, to a server.

In embodiments, in response to detecting a network downtime, kiosk may switch into an offline mode and disable one or more functions. In offline mode, automated diagnostic and treatment system 102 may inform a user of its unavailability and disable access to one or more groups of users (e.g., continuing to allow doctor access). In one mode of operation, automated diagnostic and treatment system 102 may limit user access to one or more kiosks.

Doctors may login to the system and view patient medical data, patient statistical data, and patient answers to questions, a trust score, and images of the patient applying medical sensors and taking measurements. Doctor interface station 104 allows doctors to view patients' usage information, look up any measurements or answers provided by a patient, review predicted illnesses, select an illness and review recommended treatments for such illness, review generated doctor notes and codes, and approve notes made to automated diagnostic and treatment system 102. Operation managers may be assigned to one or more kiosks to perform certain functions, such as determining permission levels for users, viewing logs of doctor/nurse actions, resetting account passwords, enabling or disabling specific kiosks, and assigning statuses to kiosks. Administrators (e.g., web administrators) may be in charge of operation managers and may assign to a user the role of operation manager. Administrators may have access to all non-medical logs related to the system as well as the ability to enable/ disable kiosks, and determine the number and type of services that are activated in a given location or region.

In embodiments, an administrator interface (not shown) may provide a list of actions taken at kiosk to a system administrator, and a list of doctors available to each operations manager or to an automated scheduling system. An action may ask for confirmation and add the operation to an immutable log. An operations manager may be trained to add and remove access rights to doctors at kiosk and to securely close a session at kiosk e.g., in response to identifying a potential issue. A system administrator may remove or add operations managers, doctors, and their access privileges. HIPAA requirements and network security requirements may be implemented to constrain how a kiosk can access medical records and handle/store user data.

Medical instrument equipment 108 is designed to collect mainly diagnostic patient data, and may comprise one or more diagnostic medical devices, for example, in a home diagnostic medical kit that generates diagnostic data based on physical and non-physical characteristics of a patient. It is noted that diagnostic system 100 may comprise additional sensors and devices that, in operation, collect, process, or transmit characteristic information about the patient, medical instrument usage, orientation, environmental parameters such as ambient temperature, humidity, location, and other useful information that may be used to accomplish the objectives of the present invention.

In operation, a patient may enter patient-related data, such as health history, patient characteristics, details about type and duration of symptoms, health concerns, medical instrument measured diagnostic data, images, and sound patterns, or other relevant information into patient interface station 106, e.g., at an exemplary landing screen. The patient may use any means of communication, such as voice control, to enter data, e.g., in the form of a machine-driven questionnaire. Patient interface station 106 may provide the data raw or in processed form to automated diagnostic and treatment system 102, e.g., via a secure communication.

In embodiments, the patient may be prompted, e.g., by a software application, to answer questions intended to aid in the diagnosis of one or more medical conditions. The software application may provide guidance by describing how to use medical instrument equipment 108 to administer a diagnostic test or how to make diagnostic measurements for any particular device that may be part of medical instrument equipment 108 so as to facilitate accurate measurements of patient diagnostic data.

In embodiments, the patient may use medical instrument equipment 108 to create a patient health profile that serves as a baseline profile. Gathered patient-related data may be securely stored in database 103 or a secure remote server (not shown) coupled to automated diagnostic and treatment system 102. In embodiments, automated diagnostic and treatment system 102 enables interaction between a patient and a remotely located health care professional, who may provide instructions to the patient, e.g., by communicating via the software application. A doctor may log into a cloud-based system (not shown), via doctor interface station 104, in order to access and retrieve patient-related data, e.g., in from patent file that may comprise, videos, audio clips, and images, e.g., via a reference link in the patient's file. In embodiments, automated diagnostic and treatment system 102 presents automated diagnostic suggestions to a doctor, who may verify or modify the suggested information.

In embodiments, based on one more patient questionnaires, data gathered by medical instrument equipment 108, patient feedback, and historic diagnostic information, the patient may be provided with instructions, feedback, results 122, and other information pertinent to the patient's health. In embodiments, the doctor may select an illness based on automated diagnostic system suggestions and/or follow a sequence of instructions, feedback, and/or results 122 may be adjusted based on decision vectors associated with a medical database. In embodiments, automated diagnostic and treatment system 102 uses the decision vectors to generate a diagnostic result, e.g., in response to patient answers and/or measurements of the patient's vital signs.

In embodiments, medical instrument equipment 108 comprises a number of sensors, such as accelerometers, gyroscopes, pressure sensors, cameras, bolometers, altimeters, IR LEDs, and proximity sensors that may be coupled to one or more medical devices, e.g., a thermometer, to assist in performing diagnostic measurements and/or monitor a patient's use of medical instrument equipment 108 for accuracy. A camera, bolometer, or other spectrum imaging device (e.g. radar), in addition to taking pictures of the patient, may use image or facial recognition software and machine vision to recognize body parts, items, and actions to aid the patient in locating suitable positions for taking a measurement on the patient's body, e.g., by identifying any part of the patient's body as a reference.

Examples of the types of diagnostic data that medical instrument equipment 108 may generate comprise body temperature, blood pressure, images, sound, heart rate, blood oxygen level, motion, ultrasound, pressure or gas analysis, continuous positive airway pressure, electrocardiogram, electroencephalogram, Electrocardiography, BMI, muscle mass, blood, urine, and any other patient-related data 128. In embodiments, patient-related data 128 may be derived from a non-surgical wearable or implantable monitoring device that gathers sample data.

In embodiments, an IR LED, proximity beacon, or other identifiable marker (not shown) may be attached to medical instrument equipment 108 to track the position and placement of medical instrument equipment 108. In embodiments, a camera, bolometer, or other spectrum imaging device uses the identifiable marker as a control tool to aid the camera or the patient in determining the position of medical instrument equipment 108.

In embodiments, machine vision software may use real-time video processing to track and overlay or superimpose, e.g., on a screen, the position of the identifiable marker e.g., IR LED, heat source, or reflective material with a desired target location at which the patient should place medical instrument equipment 108, thereby, assisting the patient to properly place or align a sensor when taking medical self-measurements to ensure accurate and reliable readings. Once medical instrument equipment 108, e.g., a stethoscope is placed at the desired target location on a patient's torso, the patient may be prompted by optical or visual cues to breath according to instructions or perform other actions to facilitate medical measurements and to start a measurement.

In embodiments, one or more sensors that may be attached to medical instrument equipment 108 monitor the placement and usage of medical instrument equipment 108 by periodically or continuously recording data and comparing measured data, such as location, movement, and angles, to an expected data model and/or an error threshold to ensure measurement accuracy. A patient may be instructed to adjust an angle, location, or motion of medical instrument equipment 108, e.g., to adjust its state and, thus, avoid low-accuracy or faulty measurement readings. In embodiments, sensors attached or tracking medical instrument equipment 108 may generate sensor data and patient interaction activity data that may be compared, for example, against an idealized patient medical instrument equipment usage sensor model data to create an equipment usage accuracy score. The patient medical instrument equipment measured medical data may also be compared with idealized device measurement data expected from medical instrument equipment 108 to create a device accuracy score.

Feedback from medical instrument equipment 108 (e.g., sensors, proximity, camera, etc.) and actual device measurement data may be used to instruct the patient to properly align medical instrument equipment 108 during a measurement. In embodiments, medical instrument equipment type and sensor system monitoring of medical instrument equipment 108 patient interaction may be used to create a device usage accuracy score for use in a medical diagnosis algorithm. Similarly, patient medical instrument equipment measured medical data may be used to create a measurement accuracy score for use by the medical diagnostic algorithm.

In embodiments, machine vision software may be used to show on a monitor an animation that mimics a patient's movements and provides detailed interactive instructions and real-time feedback to the patient. This aids the patient in correctly positioning and operating medical instrument equipment 108 relative to the patient's body so as to ensure a high level of accuracy when using medical instrument equipment 108 is operated.

In embodiments, once automated diagnostic and treatment system 102 detects unexpected data, e.g., data representing an unwanted movement, location, measurement data, etc., a validation process comprising a calculation of a trustworthiness score or reliability factor is initiated in order to gauge the measurement accuracy. Once the accuracy of the measured data falls below a desired level or is otherwise deemed inaccurate or not trustworthy, the patient may be given instructions, e.g., by displaying a message, to either repeat a measurement or request assistance by an assistant, who may answer questions, e.g., remotely via an application to help with proper equipment usage and other technical issues, or alert a nearby person to assist with using medical instrument equipment 108. The validation process, may also instruct a patient to answer additional questions, and may comprise calculating the measurement accuracy score based on a measurement or re-measurement.

In embodiments, upon request 124, automated diagnostic and treatment system 102 may enable a patient-doctor interaction by granting the patient and doctor access to diagnostic system 100. The patient may enter data, take measurements, and submit images and audio files or any other information to the application or web portal. The doctor may access that information, for example, to review a diagnosis generated by automated diagnostic and treatment system 102, and generate, confirm, or modify instructions for the patient. Patient-doctor interaction, while not required for diagnostic and treatment, if used, may occur in person, real-time via an audio/video application, or by any other means of communication.

In embodiments, automated diagnostic and treatment system 102 may utilize images generated from a diagnostic examination of mouth, throat, eyes, ears, skin, extremities, surface abnormalities, internal imaging sources, and other suitable images and/or audio data generated from diagnostic examination of heart, lungs, abdomen, chest, joint motion, voice, and any other audio data sources. Automated diagnostic and treatment system 102 may further utilize patient lab tests, medical images, or any other medical data. In embodiments, automated diagnostic and treatment system 102 enables medical examination of the patient, for example, using medical devices, e.g., ultrasound, in medical instrument equipment 108 to detect sprains, contusions, or fractures, and automatically provide diagnostic recommendations regarding a medical condition of the patient.

In embodiments, diagnosis comprises the use of medical database decision vectors that are at least partially based on the patient's self-measured (or assistant-measured) vitals or other measured medical data, the accuracy score of a measurement dataset, a usage accuracy score of a sensor attached to medical instrument equipment 108, a regional illness trend, and information used in generally accepted medical knowledge evaluations steps. The decision vectors and associated algorithms, which may be installed in automated diagnostic and treatment system 102, may utilize one or more-dimensional data, patient history, patient questionnaire feedback, and pattern recognition or pattern matching for classification using images and audio data. In embodiments, a medical device usage accuracy score generator (not shown) may be implemented within automated diagnostic and treatment system 102 and may utilize an error vector of any device in medical instrument equipment or attached sensors 108 to create the device usage accuracy score and utilize the actual patient-measured device data to create the measurement data accuracy score.

In embodiments, automated diagnostic and treatment system 102 outputs diagnosis and/or treatment information that may be communicated to the patient, for example, electronically or in person by a medical professional, e.g., a treatment guideline that may include a prescription for a medication. In embodiments, prescriptions may be communicated directly to a pharmacy for pick-up or automated home delivery.

In embodiments, automated diagnostic and treatment system 102 may generate an overall health risk profile of the patient and recommend steps to reduce the risk of overlooking critical conditions or guide the patient to a nearby health care that can treat the potentially dangerous condition. The health risk profile may assist a treating doctor in fulfilling duties to the patient, for example, to carefully review and evaluate the patient and, if deemed necessary, refer the patient to a specialist, initiate further testing, etc. The health risk profile advantageously reduces the potential for negligence and, thus, medical malpractice.

Automated diagnostic and treatment system 102, in embodiments, comprises a payment feature that uses patient identification information to access a database to, e.g., determine whether a patient has previously arranged a method of payment, and if the database does not indicate a previously arranged method of payment, automated diagnostic and treatment system 102 may prompt the patient to enter payment information, such as insurance, bank, or credit card information. Automated diagnostic and treatment system 102 may determine whether payment information is valid and automatically obtain an authorization from the insurance, EHR system, and/or the card issuer for payment for a certain amount for services rendered by the doctor. An invoice may be electronically presented to the patient, e.g., upon completion of a consultation, such that the patient can authorize payment of the invoice, e.g., via an electronic signature. In embodiments, information transmitted to the database may be considered immutable and request that modifications are made into new records referenced by a user's unique ID.

In embodiments, patient database 103 (e.g., a secured cloud-based database) may comprise a security interface (not shown) that allows secure access to a patient database, for example, by using patient identification information to obtain the patient's medical history. The interface may utilize biometric, bar code, or other electronically security methods. In embodiments, medical instrument equipment 108 uses unique identifiers that are used as a control tool for measurement data. Database 103 may be a repository for any type of data created, modified, or received by diagnostic system 100, such as generated diagnostic information, information received from patient's wearable electronic devices, remote video/audio data and instructions, e.g., instructions received from a remote location or from the application.

In embodiments, fields in the patient's electronic health care record (EHR) are automatically populated based on one or more of questions asked by diagnostic system 100, measurements taken by the patient/system 100, diagnosis and treatment codes generated by system 100, one or more trust scores, and imported patient health care data from one or more sources, such as an existing health care database. It is understood the format of imported patient health care data may be converted to be compatible with the EHR format of system 100. Conversely, exported patient health care data may be converted, e.g., to be compatible with an external EHR database.

In addition, patient-related data documented by system 100 provide support for the code decision for the level of exam a doctor performs. Currently, for billing and reimbursement purposes, doctors have to select one out of a large number of existing medical codes (e.g., ICD10 currently holds approximately 97,000 codes) to identify an illness and provide an additional code to identify the level of physical exam/diagnosis performed (e.g., full body physical exam) based on an identified illness.

In embodiments, patient answers are used to suggest to the doctor a level of exam that is supported by the identified illness, e.g., to ensure that the doctor does not perform unnecessary in-depth exams for minor illnesses or a treatment that may not be covered by the patient's insurance.

In embodiments, upon identifying a diagnosis, system 100 generates one or more recommendations/suggestions/options for a particular treatment. In embodiments, one or more treatment plans are generated that the doctor may discuss with the patient and decide on a suitable treatment. For example, one treatment plan may be tailored purely for medical effectiveness, and another one may consider the cost of available drugs. In embodiments, system 100 may generate a prescription or lab test request and consider factors, such as recent research results, available drugs and possible drug interactions, the patient's medical history, traits of the patient, family history, and any other factors that may affect treatment when providing treatment information. In embodiments, diagnosis and treatment databases may be continuously updated, e.g., by health care professionals, so that an optimal treatment may be administered to a particular patient, e.g., a patient identified as member of a certain risk group.

It is noted that sensors and measurement techniques may be advantageously combined to perform multiple functions using a reduced number of sensors. For example, an optical sensor may be used as a thermal sensor by utilizing IR technology to measure body temperature. It is further noted that some or all data collected by system 100 may be processed and analyzed directly within automated diagnostic and treatment system 102 or transmitted to an external device (e.g., reading device not shown in FIG. 1) for further processing and analysis, e.g., to enable additional diagnostics.

In embodiments, automated diagnostic and treatment system 102 may automatically connect to a VPN that may be shared between a server and other automated diagnostic systems or kiosks, which may be set to reject packets outside the VPN using IPtables.

Figure 2:
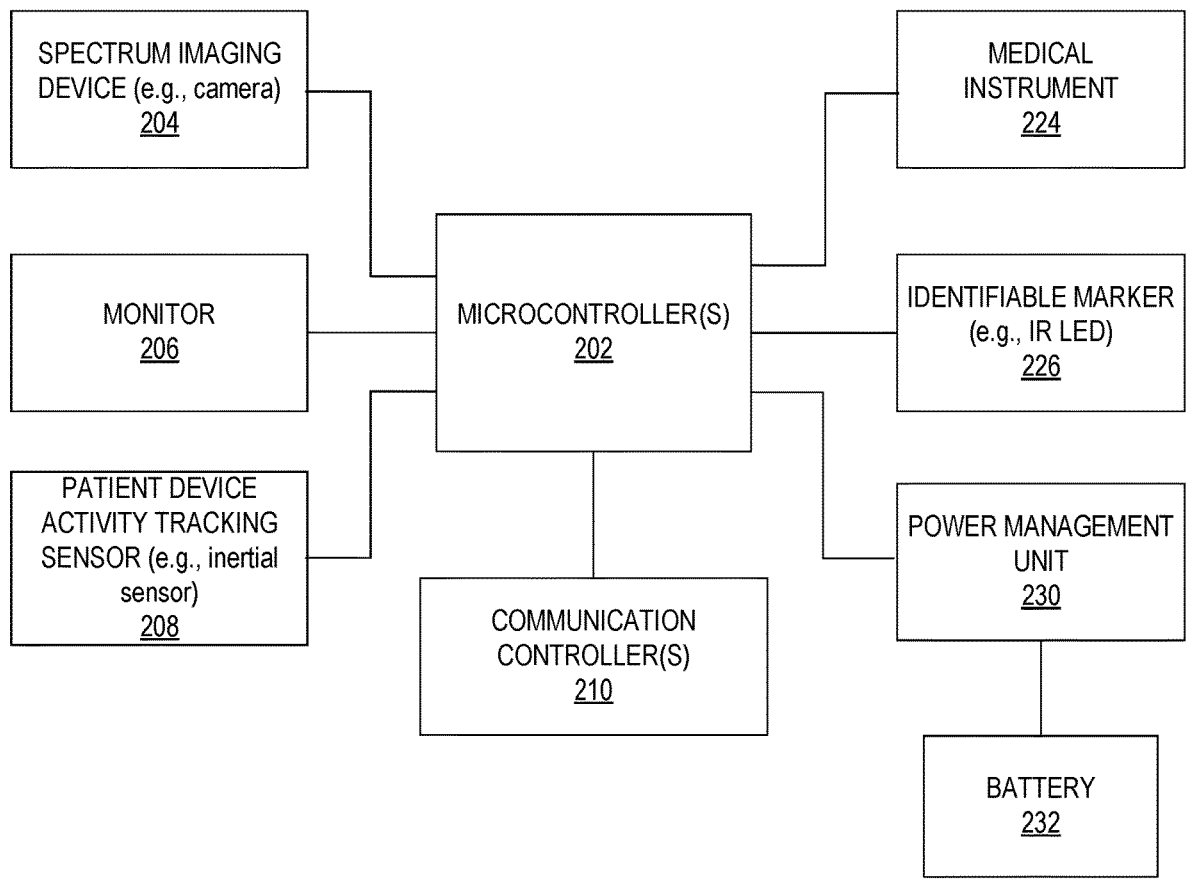
FIG. 2 illustrates an exemplary patient diagnostic measurement system according to embodiments of the present disclosure.

FIG. 2 illustrates an exemplary patient diagnostic measurement system according to embodiments of the present disclosure. As depicted, patient diagnostic measurement system 200 comprises microcontroller 202, spectrum imaging device, e.g., camera 204, monitor 206, patient-medical equipment activity tracking sensors 208, e.g., an inertial sensor, communications controller 210, medical instruments 224, identifiable marker 226, e.g., an IR LED, power management unit 230, and battery 232. Each component may be coupled directly or indirectly by electrical wiring, wirelessly, or optically to any other component in system 200.

Medical instrument 224 comprises one or more devices that are capable of measuring physical and non-physical characteristics of a patient that, in embodiments, may be customized according to varying anatomies among patients, irregularities on a patient's skin, and the like. In embodiments, medical instrument 224 is a combination of diagnostic medical devices that generate diagnostic data based on patient characteristics. Exemplary diagnostic medical devices are heart rate sensors, otoscopes, digital stethoscopes, in-ear thermometers, blood oxygen sensors, high-definition cameras, spirometers, blood pressure meters, respiration sensors, skin resistance sensors, glucometers, ultrasound devices, electrocardiographic sensors, body fluid sample collectors, eye slit lamps, weight scales, and any devices known in the art that may aid in performing a medical diagnosis. In embodiments, patient characteristics and vital signs data may be received from and/or compared against wearable or implantable monitoring devices that gather sample data, e.g., a fitness device that monitors physical activity.

One or more medical instruments 224 may be removably attachable directly to a patient's body (e.g., torso) via patches or electrodes that may use adhesion to provide good physical or electrical contact. In embodiments, medical instruments 224 (e.g., a contact-less thermometer) may perform contact-less measurements some distance away from the patient's body.

In embodiments, microcontroller 202 is a secure microcontroller that securely communicates information in encrypted form to ensure privacy and the authenticity of measured data. activity sensor, patient-equipment proximity information, and other information in patient diagnostic measurement system 200. This may be accomplished by taking advantage of security features embedded in hardware of microcontroller 202 and/or software that enable security features during transit and storage of sensitive data. Each device in patient diagnostic measurement system 200 may have keys that handshake to perform authentication operations on a regular basis.

Spectrum imaging device 204 is any audio/video device that may capture patient images and sound at any frequency or image type. Monitor 206 is any screen or display device that may be coupled to camera, sensors and/or any part of system 200. Patient-equipment activity tracking sensor 208 may be any single or multi-dimensional sensor, such as an accelerometer, a multi-axis gyroscope, pressure sensor, and a magnetometer capable of providing position, motion, pressure on medical equipment or orientation data based on patient interaction. In embodiments, one or more sensors comprise an accelerometer that generates location data that can be exchanged with another patient diagnostic measurement system and/or server.

Patient-equipment activity tracking inertial sensor 208 may be attached to (removably or permanently) or embedded into medical instrument 224. Identifiable marker IR LED 226 represents any device, heat source, reflective material, proximity beacon, altimeter, etc., that may be used by microcontroller 202 as an identifiable marker. Like patient-equipment activity tracking inertial sensor 208, identifiable marker IR LED 226 may be reattacheable to or embedded into medical instrument 224.

In embodiments, communication controller 210 is a wireless communications controller attached either permanently or temporarily to medical instrument 224 or the patient's body to establish a bi-directional wireless communications link and transmit processed and unprocessed data, e.g., between sensors and microcontroller 202 by using any wireless communication protocol known in the art, such as Bluetooth Low Energy, e.g., via an embedded antenna circuit that wirelessly communicates the data. One of ordinary skill in the art will appreciate that electromagnetic fields generated by such an antenna circuit may be of any suitable type. For example, in case of an RF field, the operating frequency may be located in the ISM frequency band, e.g., 13.56 MHz. In embodiments, data received by wireless communications controller 210 may be forwarded to a host device (not shown) that may run a software application.

In embodiments, power management unit 230 is coupled to microcontroller 202 to provide energy to, e.g., microcontroller 202 and communication controller 210. Battery 232 may be a back-up battery for power management unit 230 or a battery in any one of the devices in patient diagnostic measurement system 200. One of ordinary skill in the art will appreciate that one or more devices in system 200 may be operated from the same power source (e.g., battery 232) and perform more than one function at the same or different times. A person of skill in the art will also appreciate that one or more components, e.g., sensors 208, 226, may be integrated on a single chip/system, and that additional electronics, such as filtering elements, etc., may be implemented to support the functions of medical instrument equipment measurement or usage monitoring and tracking system 200 according to the objectives of the invention.

In operation, a patient may use medical instrument 224 to gather patient data based on physical and non-physical patient characteristics, e.g., vital signs data, images, sounds, and other information useful in the monitoring and diagnosis of a health-related condition. The patient data is processed by microcontroller 202 and may be stored in a database (not shown). In embodiments, the patient data may be used to establish baseline data for a patient health profile against which subsequent patient data may be compared.

In embodiments, patient data may be used to create, modify, or update EHR data, such as personal information, medical information, or any other patient-related data. Gathered medical instrument equipment data, along with any other patient and sensor data, may be processed directly by patient diagnostic measurement system 200 or communicated to a remote location for analysis, e.g., to diagnose existing and expected health conditions to benefit from early detection and prevention of acute conditions or aid in the development of novel medical diagnostic methods.

In embodiments, medical instrument 224 is coupled to a number of sensors, such as patient-equipment tracking inertial sensor 208 and/or identifiable marker IR LED 226, that may monitor a position/orientation of medical instrument 224 relative to the patient's body when a medical equipment measurement is taken. In embodiments, sensor data generated by sensor 208, 226 or other sensors may be used in connection with, e.g., data generated by spectrum imaging device camera 204, proximity sensors, transmitters, bolometers, or receivers to provide feedback to the patient to aid the patient in properly aligning medical instrument 224 relative to the patient's body part of interest when performing a diagnostic measurement. A person skilled in the art will appreciate that not all sensors 208, 226, beacon, pressure, altimeter, etc., need to operate at all times. Any number of sensors may be partially or completely disabled, e.g., to conserve energy.

In embodiments, the sensor emitter comprises a light signal emitted by IR LED 226 or any other identifiable marker that may be used as a reference signal. In embodiments, the reference signal may be used to identify a location, e.g., within an image and based on a characteristic that distinguishes the reference from other parts of the image. In embodiments, the reference signal is representative of a difference between the position of medical instrument 224 and a preferred location relative to a patient's body. In embodiments, spectrum imaging device camera 204 displays, e.g., via monitor 206, the position of medical instrument 224 and the reference signal at the preferred location so as to allow the patient to determine the position of medical instrument 224 and adjust the position relative to the preferred location, displayed by spectrum imaging device camera 204.

Spectrum imaging device camera 204, proximity sensor, transmitter, receiver, bolometer, or any other suitable device may be used to locate or track the reference signal, e.g., within the image, relative to a body part of the patient. In embodiments, this may be accomplished by using an overlay method that overlays an image of a body part of the patient against an ideal model of device usage to enable real-time feedback for the patient. The reference signal along with signals from other sensors, e.g., patient-equipment activity inertial sensor 208, may be used to identify a position, location, angle, orientation, or usage associated with medical instrument 224 to monitor and guide a patient's placement of medical instrument 224 at a target location and accurately activate a device for measurement.

In embodiments, e.g., upon receipt of a request signal, microcontroller 202 activates one or more medical instruments 224 to perform measurements and sends data related to the measurement back to microcontroller 202. The measured data and other data associated with a physical condition may be automatically recorded and a usage accuracy of medical instrument 224 may be monitored.

In embodiments, microcontroller 202 uses an image in any spectrum, motion signal and/or an orientation signal by patient-equipment activity inertial sensor 208 to compensate or correct the vital signs data output by medical instrument 224. Data compensation or correction may comprise filtering out certain data as likely being corrupted by parasitic effects and erroneous readings that result from medical instrument 224 being exposed to unwanted movements caused by perturbations or, e.g., the effect of movements of the patient's target measurement body part.

In embodiments, signals from two or more medical instruments 224, or from medical instrument 224 and patient-activity activity system inertial sensor 208, are combined, for example, to reduce signal latency and increase correlation between signals to further improve the ability of vital signs measurement system 200 to reject motion artifacts to remove false readings and, therefore, enable a more accurate interpretation of the measured vital signs data.

In embodiments, spectrum imaging device camera 204 displays actual or simulated images and videos of the patient and medical instrument 224 to assist the patient in locating a desired position for medical instrument 224 when performing the measurement so as to increase measurement accuracy. Spectrum imaging device camera 204 may use image or facial recognition software to identify and display eyes, mouth, nose, ears, torso, or any other part of the patient's body as reference.

In embodiments, vital signs measurement system 200 uses machine vision software that analyzes measured image data and compares image features to features in a database, e.g., to detect an incomplete image for a target body part, to monitor the accuracy of a measurement and determine a corresponding score. In embodiments, if the score falls below a certain threshold system 200 may provide detailed guidance for improving measurement accuracy or to receive a more complete image, e.g., by providing instructions on how to change an angle or depth of an otoscope relative to the patient's ear.

In embodiments, the machine vision software may use an overlay method to mimic a patient's posture/movements to provide detailed and interactive instructions, e.g., by displaying a character, image of the patient, graphic, camera view, or avatar animation of actions to be performed on monitor 206 overlaid with computer vision information to provide feedback to the patient. The instructions, image, or avatar may start or stop and decide what help instruction to display based on the type of medical instrument 224, the data from spectrum imaging device camera 204, patient-equipment activity sensors inertial sensors 208, bolometer, transmitter and receiver, and/or identifiable marker IR LED 226 (an image, a measured position or angle, etc.), and a comparison of the data to idealized data. This further aids the patient in correctly positioning and operating medical instrument 224 relative to the patient's body, ensures a high level of accuracy when operating medical instrument 224, and solves potential issues that the patient may encounter when using medical instrument 224.

In embodiments, instructions may be provided via monitor 206 and describe in audio/visual format and in any desired level of detail, how to use medical instrument 224 to perform a diagnostic test or measurement, e.g., how to take temperature, so as to enable patients to perform measurements of clinical-grade accuracy. In embodiments, monitor 206 may indicate, e.g., via a title label on the top of a screen or in an instructional window, the test being performed (e.g., heart rate sensor/pulse oximeter, taking temperature). A monitor layout may comprise various views, such as an instruction view, silhouette view, avatar view, and camera view that may be automatically activated based on the patient interaction, for example, after a measurement has been taken by the user. Monitor 206 may also provide an interface for displaying illness probabilities, probability score listing, and other statistics to a user. In embodiments, patient data (measurement data, videos, images, audio, etc.) may be sent to a server that further processes and/or stores the data.

In embodiments, each sensor 208, 226, e.g., proximity, bolometer, transmitter/receiver may be associated with a device usage accuracy score. A device usage accuracy score generator (not shown), which may be implemented in microcontroller 202, may use the sensor data to generate a medical instrument usage accuracy score that is representative of the reliability of medical instrument 224 measurement on the patient. In embodiments, the score may be based on a difference between an actual position of medical instrument 224 and a preferred position. In addition, the score may be based on detecting a motion, e.g., during a measurement. In embodiments, in response to determining that the accuracy score falls below a threshold, a repeat measurement or device usage assistance may be requested. In embodiments, the device usage accuracy score is derived from an error vector generated for one or more sensors 208, 226. The resulting device usage accuracy score may be used when generating or evaluating medical diagnosis data.

In embodiments, microcontroller 202 analyzes the patient measured medical instrument data to generate a trust score indicative of the acceptable range of the medical instrument. For example, by comparing the medical instrument measurement data against reference measurement data or reference measurement data that would be expected from medical instrument 224. As with device usage accuracy score, the trust score may be used when generating or evaluating a medical diagnosis data.

Figure 3:
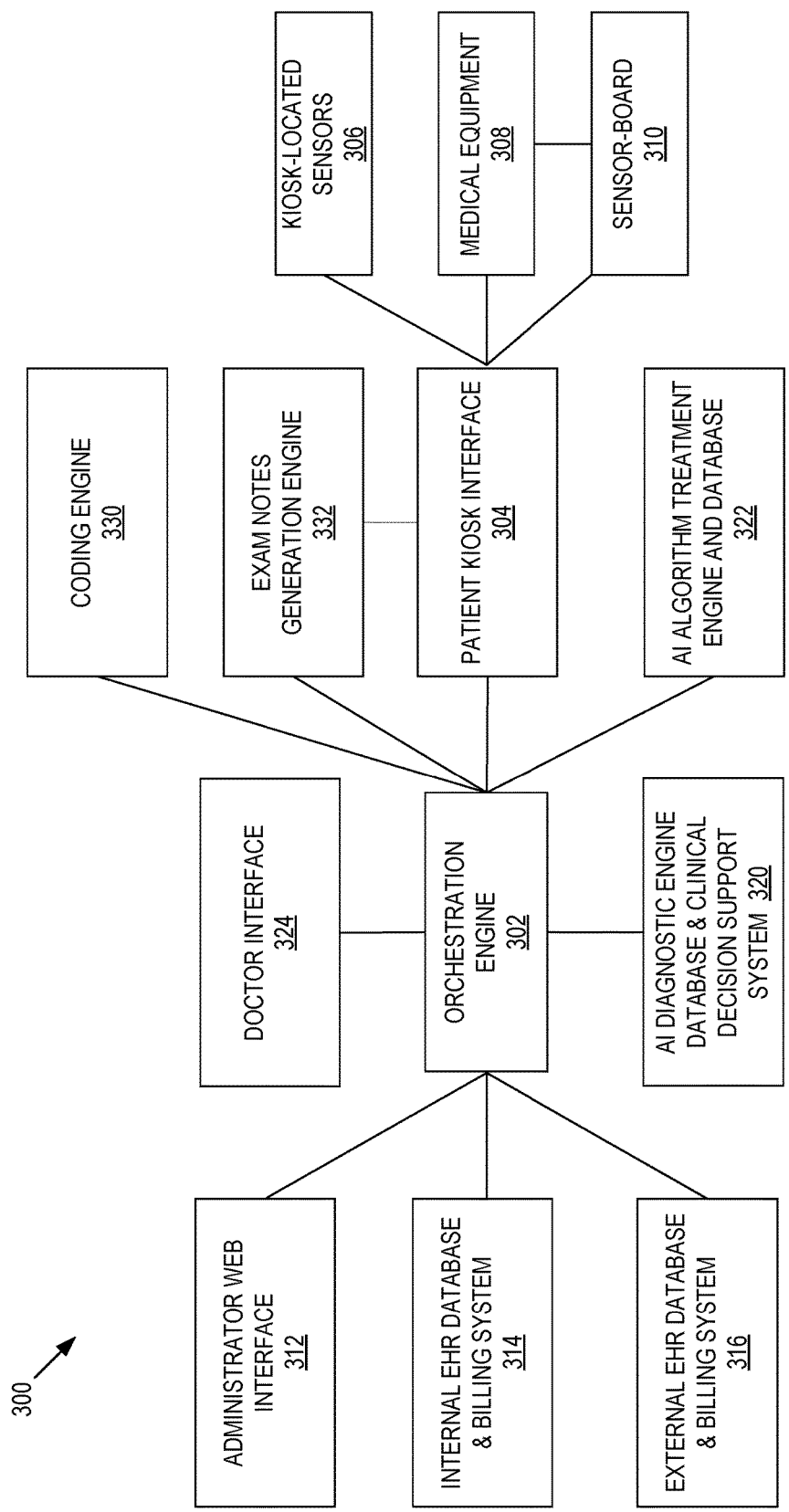
FIG. 3 illustrates an exemplary medical data system according to embodiments of the present disclosure.

FIG. 3 illustrates an exemplary medical data system according to embodiments of the present disclosure. Medical data system 300 comprises main orchestration engine 302, patient kiosk interface 304, doctor interface 324, kiosk-located sensors 306, medical equipment 308, which may be coupled to sensor-board 310, administrator web interface 312, internal EHR database and billing system 314, external EHR database and billing system 316, Artificial Intelligence (AI) diagnostic engine and clinical decision support system 320, AI treatment engine and database 322, coding engine 330, and exam notes generation engine 332.

In operation, patient kiosk interface 304, which may be a touch, voice, or text interface that is implemented into a tablet, computer, mobile device, or any other electronic device, receives patient-identifiable information, e.g., via a terminal or kiosk.

In embodiments, the patient-identifiable information and/or matching patient-identifiable information may be retrieved from internal EHR database and billing system 314 or searched for and downloaded from external EHR database and billing system 316, which may be a public or private database such as a proprietary EHR database. In embodiments, if internal EHR database 314 and external EHR database 316 comprise no record for a patient, a new patient record may be created in internal EHR database and billing system 314. In embodiments, internal EHR database and billing system 314 is populated based on external EHR database 316.

In embodiments, data generated by medical equipment 308 is adjusted using measurement accuracy scores that are based on a position accuracy or reliability associated with using medical equipment 308, e.g., by applying weights to the diagnostic medical information so as to correct for systemic equipment errors or equipment usage errors. In embodiments, generating the diagnostic data comprises adjusting diagnostic probabilities based on the device accuracy scores or a patient trust score associated with a patient. The patient trust score may be based on a patient response or the relative accuracy of responses by other patients. Orchestration engine 302 may record a patient's interactions with patient-kiosk interface 304 and other actions by a patient in diagnostic EHR database and billing system 314 or external EHR database and billing system 316.

In embodiments, orchestration engine 302 coordinates gathering data from the AI diagnostic engine and clinical decision support system 320 which links gathered data to symptoms, diagnostics, and AI treatment engine and database 322 to automatically generate codes for tracking, diagnostic, follow-up, and billing purposes. Codes may comprise medical examination codes, treatment codes, procedural codes (e.g., numbers or alphanumeric codes that may be used to identify specific health interventions taken by medical professionals, such as ICPM, ICHI, and other codes that may describe a level of medical exam), lab codes, medical image codes, billing codes, pharmaceutical codes (e.g., ATC, NDC, and other codes that identify medications), and topographical codes that indicate a specific location in the body, e.g., ICD-O or SNOMED.

In embodiments, system 300 may comprise a diagnostic generation engine (not shown in FIG. 3) that may, for example, be implemented into coding engine 330. The diagnostic generation engine may generate diagnostic codes e.g., ICD-9-CM, ICD-10, which may be used to identify diseases, disorders, and symptoms. In embodiments, diagnostic codes may be used to determine morbidity and mortality.

In embodiments, generated codes may be used when generating a visit report and to update internal EHR database and billing system 314 and/or external EHR database and billing system 316. In embodiments, the visit report is exported, e.g., by using a HIPAA compliant method, to external EHR database and billing system 316. It is understood that while generated codes may follow any type of coding system and guidelines, rules, or regulations (e.g., AMA billing guidelines) specific to health care, other codes may equally be generated.

In embodiments, exam notes generation engine 332 aids a doctor in writing a report, such as a medical examination notes that may be used in a medical evaluation report. In embodiments, exam notes generation engine 332, for example in concert with AI diagnostic engine and clinical decision support system 320 and/or AI treatment engine and database 322, generates a text description of an exam associated with the patient's use of system 300, patient-doctor interaction, and diagnosis or treatment decisions resulting therefrom. Exam notes may comprise any type of information related to the patient, items examined by system 300 or a doctor, diagnosis justification, treatment option justification, and other conclusions. As an example, exam notes generation engine 332 may at least partially populate a text with notes related to patient information, diagnostic medical information, and other diagnosis or treatment options and a degree of their relevance (e.g., numerical/probabilistic data that supports a justification why a specific illness or treatment option was not selected).

In embodiments, notes comprise patient-related data such as patient interaction information that was used to make a recommendation regarding a particular diagnosis or treatment. It is understood that the amount and detail of notes may reflect the closeness of a decision and the severity of an illness. Doctor notes for treatment may comprise questions that a patient was asked regarding treatment and reasons for choosing a particular treatment and not choosing alternative treatments provided by AI treatment engine and database 322. In embodiments, provider notes may be included in a patient visit report and also be exported to populate an internal or external EHR database and billing system.

In embodiments, orchestration engine 302 forwards a request for patient-related data to patient kiosk interface 304 to solicit patient input either directly from a patient, assistant, or medical professional in the form of answers to questions or from a medical equipment measurement (e.g., vital signs). The patient-related data may be received via secure communication and stored in internal EHR database and billing system 314. It is understood that patient input may include confirmation information, e.g., for a returning patient.

In embodiments, based on an AI diagnostic algorithm, orchestration engine 302 may identify potential illnesses and request additional medical and/or non-medical (e.g., sensor) data that may be used to narrow down the number of potential illnesses and generate diagnostic probability results.

In embodiments, the diagnostic result is generated by using, for example, data from kiosk-located sensors 306, medical equipment 308, sensor board 310, patient history, demographics, and preexisting conditions stored in either the internal EHR 314 or external EHR database 316. In embodiments, orchestration engine 302, AI diagnostic engine and clinical decision support system 320, or a dedicated exam level generation engine (not shown in FIG. 3.) suggests a level of exam in association with illness risk profile and commonly accepted physical exam guidelines. Exam level, actual exams performed, illness probability, and other information may be used for provider interface checklists that meet regulatory requirements and to generate billing codes.

In embodiments, AI diagnostic engine and clinical decision support system 320, may generate a criticality score representative of probability that a particular patient will suffer a negative health effect for a period of time from non-treatment may be assigned to an illness or a combination of illnesses as related to a specific patient situation. Criticality scores may be generated by taking into account patients' demographic, medical history, and any other patient-related information. Criticality scores may be correlated to each other and normalized and, in embodiments, may be used when calculating a malpractice score for the patient. A criticality score of 1, for example, may indicate that no long-lasting negative health effect is expected from an identified illness, while a criticality score of 10 indicates that that the patient may prematurely die if the patient in fact has that illness, but the illness remains untreated.

As an example, a mid-aged patient of general good health and having weight, blood pressure, and BMI data indicating a normal or healthy range is not likely to suffer long-lasting negative health effects from non-treatment of a common cold. As a result, a criticality score of 1 may be assigned to the common cold for this patient. Similarly, the previously referred to patient is likely to suffer moderately negative health effects from non-treatment of strep throat, such that a criticality score of 4 may be assigned for strep throat. For the same patient, the identified illness of pneumonia may be assigned a criticality score of 6, and for lung cancer, the criticality score may be 9.

In embodiments, AI treatment engine and database 322 receives from AI diagnostic engine and clinical decision support system 320 diagnosis and patient-related data, e.g., in the form of a list of potential illnesses and their probabilities together with other information about a patient. Based on the diagnosis and patient-related data, AI treatment engine and database 322 may determine treatment recommendations/suggestions/options for each of the potential illness. Treatment options may comprise automatically selected medicines, instructions to the patient regarding a level of physical activities, nutrition, or other instruction, and exam requests, such as suggested patient treatment actions, lab tests, and imaging requests that may be shared with a doctor.

In embodiments, AI treatment engine and database 322 generates a customized treatment plan for a patient, for example, based on an analysis of likelihoods of success for a number of treatment options and taking into consideration a number of factors, such as possible drug interactions, side-effects (e.g., whether the patient is allergic to certain medicines), patient demographics, and the like. In embodiments, the treatment plan comprises instructions to the patient, requests for medical images and lab reports, and suggestions regarding medication. In embodiments, treatment options mat be ranked according to the likelihood of success for a particular patient.

In embodiments, AI treatment engine and database 322 is communicatively coupled to a provider application (e.g., on a tablet) to exchange treatment information with a doctor. The provider application may be used to provide the doctor with additional details on diagnosis and treatment, such as information regarding how a probability for each illness or condition is calculated and based on which symptom(s) or why certain medication was chosen as the best treatment option.

For example, once a doctor accepts a patient, a monitor may display the output of AI diagnostic engine and clinical decision support system 320 as showing a 60% probability that the patient has the common cold, 15% probability that the patient has strep throat, 15% probability that the patient has an ear infection, 5% probability that the patient has pneumonia, and a 5% probability that the patient has lung cancer. In embodiments, these probabilities are normalized, such that their sum equals 100% or some other measure that relates to the provider.

In embodiments, the doctor may select items on a monitor to access additional details such as images, measurement data, and any other patient-related information, e.g., to evaluate a treatment plan proposed by AI treatment engine and database 322.

In embodiments, AI treatment engine and database 322 may determine the risk of false negative for each illness (e.g., strep, pneumonia, and lung cancer), even if a doctor has determined that the patient has only one illness, and initiate test/lab requests, e.g., a throat swab for strep, and an x-ray for pneumonia/lung cancer that may be ordered automatically or with doctor approval, e.g., per AMA guidelines.

In embodiments, AI treatment engine and database 322 combines gathered data with symptom, diagnostic, and treatment information and generates any type of diagnostic, physical exam level, and treatment codes for continued treatment purposes, billing purposes, or to satisfy regulatory requirements and/or physician guidelines, for example using coding engine 330. In embodiments, treatment codes are based on drug information, a patient preference, a patient medical history, and the like.

In embodiments, codes, doctor notes, and a list of additional exam requirements may be included in a visit report and used to automatically update internal EHR database and billing system 314 or external EHR database and billing system 316. The visit report may then be exported, e.g., by a HIPAA compliant method, to external EHR database and billing system 316.

In embodiments, AI treatment engine and database 322 estimates when a particular treatment is predicted to show health improvements for the patient. For example, if a predicted time period during which a patient diagnosed with strep throat and receiving antibiotics should start feeling better is three days, then, on the third day, medical data system 300 may initiate a notice to the patient to solicit patient feedback to determine whether the patient's health condition, in fact, has improved as predicted.

It is understood that patients may be asked to provide feedback at any time and that patient feedback may comprise any type of inquiries related to the patient's condition. In embodiments, the inquiry comprises questions regarding the patient's perceived accuracy of the diagnosis and/or treatment. In embodiments, if the patient does not affirm the prediction, e.g., because the symptoms are worsening or a diagnosis was incorrect, the patient may be granted continued access to system 300 for a renewed diagnosis.

In embodiments, any part of the information gathered by medical data system 300 may be utilized to improve machine learning processes of AI diagnostic engine and clinical decision support system 320 and AI treatment engine and database 322 and, thus, improve diagnoses and treatment capabilities of system 300.

Figure 4:
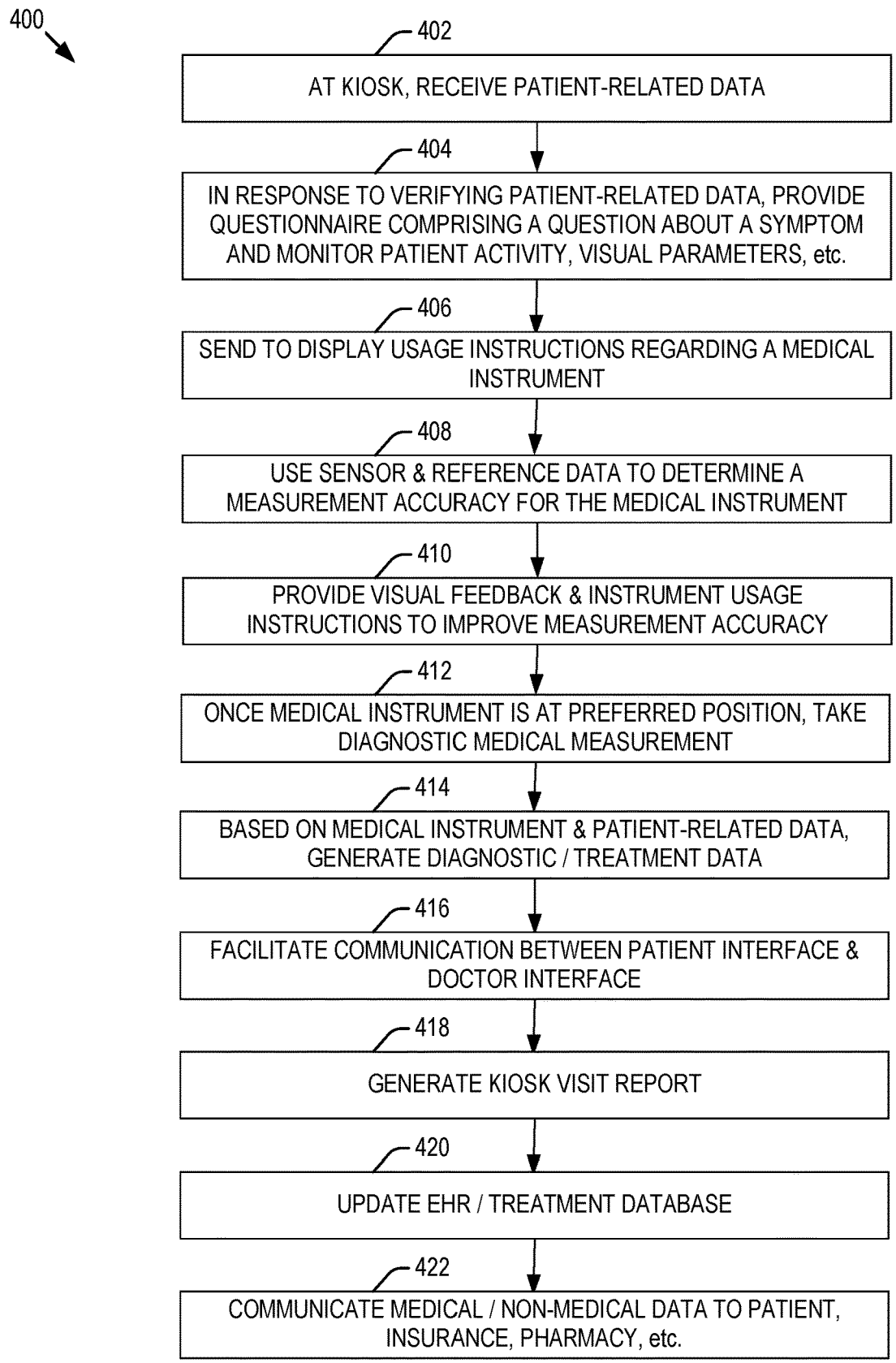
FIG. 4 is a flowchart that illustrates an exemplary process for using a medical kiosk to gather and process diagnostic medical data, according to embodiments of the present disclosure.

FIG. 4 is a flowchart that illustrates an exemplary process for using a medical kiosk to gather and process diagnostic medical data, according to embodiments of the present disclosure. Process 400 begins at step 402 when patient-related data, which may comprise non-medical patient background data (e.g., patient medical, social, criminal, and malpractice data), is received at a medical kiosk, e.g. from an external EHR database.

At step 404, once some or all of the patient-related data is verified, a patient questionnaire comprising a question about a medical symptom is communicated to a patient interface. In addition, kiosk cameras and other spectrum sensors may be used to monitor patient activity, color of skin, and other parameters that may be used in determining patient wellness.

At step 406, in response to receiving answers to the questions, an initial set of instructions may be sent to the patient interface, for example, displayed on a monitor or a tablet. In embodiments, the instructions comprise information on how to use a medical instrument (e.g., a device in a diagnostic kit) coupled to the kiosk, so diagnostic medical data, e.g., vital signs data related to the symptom, can be gathered.

In embodiments, a patient's actions and body parts of interest are recorded and displayed to a preferred location of the medical instrument to provide real-time feedback.

At step 408, based on sensor data (e.g., inertial sensor data) and/or reference data, a measurement accuracy for the medical instrument is determined.

At step 410, instrument usage instructions may be provided on how to improve measurement accuracy, e.g., using visual feedback.

At step 412, once the medical instrument is placed at a desired location, a diagnostic medical measurement can be made. It is understood that follow-up questions may be asked and additional diagnostic medical measurement data may be requested, e.g., in an iterative manner.

At step 414, diagnostic data and treatment data may be generated, based at least in part on the diagnostic medical data and the patient answers. In embodiments, a diagnosis is compared with one or more diagnoses in a treatment database to generate a suggested level of exam, a treatment recommendation, e.g., based on a diagnosis code or treatment code. In embodiments, the diagnosis adjusted, for example, based on weighted medical instrument accuracy scores or patient trust scores, which may be based on patients' manner of answering certain questions. The diagnosis may be adjusted by a machine learning process that may generate or modify any type data processed by the kiosk.

At step 416, a secure communication may be facilitated between the patient interface and a doctor interface. In embodiments, for example in an urgent care setting, the communication may be used to request on-site assistance or call a doctor.

At step 418, a kiosk visit report is generated. In embodiments, payment data, prescription data, and other patient-related data may be communicated to the patient, the patient's insurance provider, and the patient's pharmacy.

At step 420, an EHR database and/or a treatment database is updated, e.g., with a patient-specific health risk profile. Updates and adjustments may occur at certain intervals or upon the happening of an event, such as a change in certain patient data.

At step 422, medical and/or non-medical data (e.g., to patient, insurance, pharmacy, etc.) may be communicated, to the patient, the patient's insurance, a pharmacy, etc.

It is understood that local data may be erased after a visit is completed to avoid local data storage in compliance with regulations such as HIPAA. It is further understood that a patient's actions and interactions with the kiosk may be recorded and stored as part of an EHR.

One skilled in the art will recognize that: (1) certain steps may optionally be performed; (2) steps may not be limited to the specific order set forth herein; and (3) certain steps may be performed in different orders; and (4) certain steps may be done concurrently.

In embodiments, one or more computing systems, such as mobile/tablet/computer or the automated diagnostic system, may be configured to perform one or more of the methods, functions, and/or operations presented herein. Systems that implement at least one or more of the methods, functions, and/or operations described herein may comprise an application or applications operating on at least one computing system. The computing system may comprise one or more computers and one or more databases. The computer system may be a single system, a distributed system, a cloud-based computer system, or a combination thereof.

It shall be noted that the present disclosure may be implemented in any instruction-execution/computing device or system capable of processing data, including, without limitation phones, laptop computers, desktop computers, and servers. The present disclosure may also be implemented into other computing devices and systems. Furthermore, aspects of the present disclosure may be implemented in a wide variety of ways including software (including firmware), hardware, or combinations thereof. For example, the functions to practice various aspects of the present disclosure may be performed by components that are implemented in a wide variety of ways including discrete logic components, one or more application specific integrated circuits (ASICs), and/or program-controlled processors. It shall be noted that the manner in which these items are implemented is not critical to the present disclosure.

Figure 5:
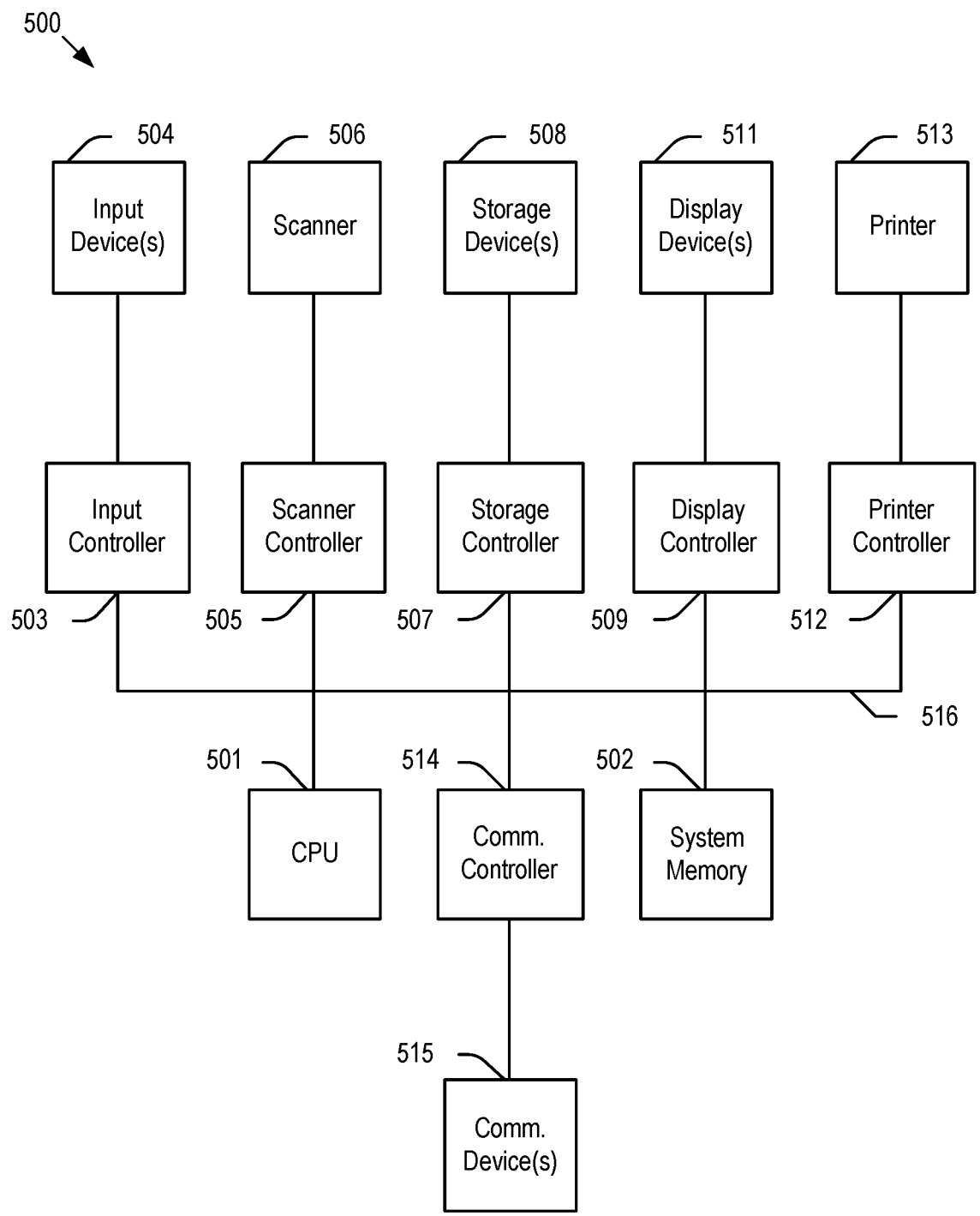
FIG. 5 depicts a simplified block diagram of a computing device/information handling system according to embodiments of the present disclosure.

Having described the details of the disclosure, an exemplary system that may be used to implement one or more aspects of the present disclosure is described next with reference to FIG. 5. Each of patient interface station 106 and automated diagnostic system 102 in FIG. 1 may comprise one or more components in the system 500. As illustrated in FIG. 5, system 500 includes a central processing unit (CPU) 501 that provides computing resources and controls the computer. CPU 501 may be implemented with a microprocessor or the like, and may also include a graphics processor and/or a floating point coprocessor for mathematical computations. System 500 may also include a system memory 502, which may be in the form of random-access memory (RAM) and read-only memory (ROM).

A number of controllers and peripheral devices may also be provided, as shown in FIG. 5. An input controller 503 represents an interface to various input device(s) 504, such as a keyboard, mouse, or stylus. There may also be a scanner controller 505, which communicates with a scanner 506. System 500 may also include a storage controller 507 for interfacing with one or more storage devices 508 each of which includes a storage medium such as magnetic tape or disk, or an optical medium that might be used to record programs of instructions for operating systems, utilities and applications which may include embodiments of programs that implement various aspects of the present disclosure. Storage device(s) 508 may also be used to store processed data or data to be processed in accordance with the disclosure. System 500 may also include a display controller 509 for providing an interface to a display device 511, which may be a cathode ray tube (CRT), a thin film transistor (TFT) display, or other type of display. System 500 may also include a printer controller 512 for communicating with a printer 55. A communications controller 514 may interface with one or more communication devices 515, which enables system 500 to connect to remote devices through any of a variety of networks including the Internet, an Ethernet cloud, an FCoE/DCB cloud, a local area network (LAN), a wide area network (WAN), a storage area network (SAN) or through any suitable electromagnetic carrier signals including infrared signals.

In the illustrated system, all major system components may connect to a bus 516, which may represent more than one physical bus. However, various system components may or may not be in physical proximity to one another. For example, input data and/or output data may be remotely transmitted from one physical location to another. In addition, programs that implement various aspects of this disclosure may be accessed from a remote location (e.g., a server) over a network. Such data and/or programs may be conveyed through any of a variety of machine-readable medium including, but are not limited to: magnetic media such as hard disks, floppy disks, and magnetic tape; optical media such as CD-ROMs and holographic devices; magneto-optical media; and hardware devices that are specially configured to store or to store and execute program code, such as application specific integrated circuits (ASICs), programmable logic devices (PLDs), flash memory devices, and ROM and RAM devices.

Embodiments of the present disclosure may be encoded upon one or more non-transitory computer-readable media with instructions for one or more processors or processing units to cause steps to be performed. It shall be noted that the one or more non-transitory computer-readable media shall include volatile and non-volatile memory. It shall be noted that alternative implementations are possible, including a hardware implementation or a software/hardware implementation. Hardware-implemented functions may be realized using ASIC(s), programmable arrays, digital signal processing circuitry, or the like. Accordingly, the "means" terms in any claims are intended to cover both software and hardware implementations. Similarly, the term "computer-readable medium or media" as used herein includes software and/or hardware having a program of instructions embodied thereon, or a combination thereof. With these implementation alternatives in mind, it is to be understood that the figures and accompanying description provide the functional information one skilled in the art would require to write program code (i.e., software) and/or to fabricate circuits (i.e., hardware) to perform the processing required.

It shall be noted that embodiments of the present disclosure may further relate to computer products with a non-transitory, tangible computer-readable medium that have computer code thereon for performing various computer-implemented operations. The media and computer code may be those specially designed and constructed for the purposes of the present disclosure, or they may be of the kind known or available to those having skill in the relevant arts. Examples of tangible computer-readable media include, but are not limited to: magnetic media such as hard disks, floppy disks, and magnetic tape; optical media such as CD-ROMs and holographic devices; magneto-optical media; and hardware devices that are specially configured to store or to store and execute program code, such as application specific integrated circuits (ASICs), programmable logic devices (PLDs), flash memory devices, and ROM and RAM devices. Examples of computer code include machine code, such as produced by a compiler, and files containing higher level code that are executed by a computer using an interpreter. Embodiments of the present disclosure may be implemented in whole or in part as machine-executable instructions that may be in program modules that are executed by a processing device. Examples of program modules include libraries, programs, routines, objects, components, and data structures. In distributed computing environments, program modules may be physically located in settings that are local, remote, or both.

For purposes of this disclosure, an information handling system may include any instrumentality or aggregate of instrumentalities operable to compute, calculate, determine, classify, process, transmit, receive, retrieve, originate, switch, store, display, communicate, manifest, detect, record, reproduce, handle, or utilize any form of information, intelligence, or data for business, scientific, control, or other purposes. For example, an information handling system may be a personal computer (e.g., desktop or laptop), tablet computer, mobile device (e.g., personal digital assistant (PDA) or smart phone), server (e.g., blade server or rack server), a network storage device, or any other suitable device and may vary in size, shape, performance, functionality, and price. The information handling system may include random access memory (RAM), one or more processing resources such as a central processing unit (CPU) or hardware or software control logic, ROM, and/or other types of nonvolatile memory. Additional components of the information handling system may include one or more disk drives, one or more network ports for communicating with external devices as well as various input and output (I/O) devices, such as a keyboard, a mouse, touchscreen and/or a video display. The information handling system may also include one or more buses operable to transmit communications between the various hardware components.

One skilled in the art will recognize no computing system or programming language is critical to the practice of the present disclosure. One skilled in the art will also recognize that a number of the elements described above may be physically and/or functionally separated into sub-modules or combined together.

It will be appreciated to those skilled in the art that the preceding examples and embodiment are exemplary and not limiting to the scope of the present disclosure. It is intended that all permutations, enhancements, equivalents, combinations, and improvements thereto that are apparent to those skilled in the art upon a reading of the specification and a study of the drawings are included within the true spirit and scope of the present disclosure.

I claim:

1. A medical kiosk for generating diagnostic medical data, the medical kiosk comprising:
   a medical instrument that generates diagnostic medical information related to a physical characteristic of a patient;
   a sensor coupled to the medical instrument to generate sensor data;
   a score generator coupled to the medical instrument to generate measurement accuracy data based on one of the sensor data or medical instrument reliability data;
   a monitor that, based on the measurement accuracy data, displays patient instructions on how to adjust a position of the medical instrument relative to a target location associated with a body part of the patient to increase a measurement accuracy;
   a patient interface coupled to the medical instrument, the patient interface receives patient-related data based on one of the medical instrument or a patient questionnaire that comprises questions about a symptom;
   a doctor interface coupled to the patient interface to facilitate a communication with a health care professional, the doctor interface displays the patient-related data and diagnosis-related data; and
   a diagnosis processor coupled to the medical instrument, the diagnosis processor generates a diagnosis based on the diagnostic medical information or the patient-related data and automatically generates a diagnosis code based on the diagnosis, the diagnosis processor further applies weights to the diagnostic medical information based on the measurement accuracy data to adjust one or more diagnostic probabilities.

2. The medical kiosk according to claim 1, wherein the diagnosis processor, based on the diagnosis, generates at least one of a suggested level of exam, a treatment recommendation, and a treatment code.

3. The medical kiosk according to claim 2, further comprising a verification processor coupled to the diagnosis processor, the verification processor verifies the patient information against the patient-related data to identify the patient.

4. The medical kiosk according to claim 1, further comprising a communication system designed to securely couple the diagnosis processor to an EHR database to retrieve patient information.

5. The medical kiosk according to claim 1, wherein the medical instrument is a wearable device.

6. The medical kiosk according to claim 1, further comprising a feedback device that displays on the monitor a user model that mimics movements of the patient to provide visual feedback.

7. The medical kiosk according to claim 1, wherein the diagnosis processor adjusts the diagnosis based on at least one of a device accuracy score that is representative of an accuracy of the medical instrument and a patient trust score that is associated with a patient.

8. The medical kiosk according to claim 7, wherein the patient trust score is based on one of a patient response or a relative accuracy of other patients' answers to a specific question.

9. A method for gathering and processing diagnostic medical data using a medical kiosk, the method comprising:
   receiving, at a medical kiosk, patient-related data;
   in response to verifying at least a portion of the patient-related data, providing a patient questionnaire comprising a question about a symptom;

in response to receiving a patient answer, communicating to a patient a first set of instructions comprising information on how to use a medical instrument to gather diagnostic medical data comprising vital signs data related to the symptom;

using sensor data and reference data to determine a measurement accuracy for the medical instrument;

generating a second set of instructions comprising information on how to improve the measurement accuracy;

in response to receiving the diagnostic medical data, generating a diagnosis, based at least in part on the diagnostic medical data and the patient answer;

based on the diagnosis, automatically generating a diagnosis code;

applying weights to the diagnostic medical data based on the measurement accuracy for the medical instrument to adjust one or more diagnostic probabilities;

facilitating a communication between a doctor interface and a patient interface; and generating a visit report.

10. The method according to claim 9, further comprising recording a patient and displaying on a monitor a preferred location relative to the patient to provide real-time feedback.

11. The method according to claim 9, further comprising communicating one of payment data, prescription data, and the patient-related data to one of a patient, an insurance provider, and a pharmacy.

12. The method according to claim 9, further comprising retrieving patient information from an EHR database.

13. The method according to claim 9, further comprising comparing at least one diagnosis with one or more diagnoses in a treatment database to generate at least one of a suggested level of exam, a treatment recommendation, the diagnosis code, or a treatment code.

14. The method according to claim 9, wherein receiving the patient-related data comprises connecting to an external database to receive patient background data.

15. The method according to claim 14, wherein patient background data comprises malpractice risk data.

16. The method according to claim 9, wherein the sensor data comprises inertial sensor data.

17. The method according to claim 9, further comprising using the diagnostic medical data to update one of an EHR database or a treatment database.

18. The method according to claim 9, further comprising, using the diagnostic medical data to generate one of a health risk profile and a baseline health profile.

19. The method according to claim 9, further comprising applying a security algorithm to the medical instrument, the patient-related data, and the sensor data.

* * * * *